US008613285B2

(12) United States Patent
Fuisz

(10) Patent No.: US 8,613,285 B2
(45) Date of Patent: Dec. 24, 2013

(54) EXTRUDABLE AND EXTRUDED COMPOSITIONS FOR DELIVERY OF BIOACTIVE AGENTS, METHOD OF MAKING SAME AND METHOD OF USING SAME

(75) Inventor: Richard C. Fuisz, Beverly Hills, CA (US)

(73) Assignee: Philip Morris Products S.A., Neuchatel (CH)

( * ) Notice: Subject to any disclaimer, the term of this patent is extended or adjusted under 35 U.S.C. 154(b) by 353 days.

(21) Appl. No.: 12/757,936

(22) Filed: Apr. 9, 2010

(65) Prior Publication Data

US 2010/0247612 A1    Sep. 30, 2010

Related U.S. Application Data

(63) Continuation of application No. 12/122,201, filed on May 16, 2008, and a continuation of application No. PCT/US2008/011634, filed on Oct. 10, 2008.

(60) Provisional application No. 60/979,169, filed on Oct. 11, 2007, provisional application No. 60/990,381, filed on Nov. 27, 2007, provisional application No. 61/054,195, filed on May 19, 2008.

(30) Foreign Application Priority Data

Oct. 2, 2008    (WO) ................ PCT/US2008/011374

(51) Int. Cl.
*A24B 15/00* (2006.01)
(52) U.S. Cl.
USPC .......................................... 131/352; 131/347
(58) Field of Classification Search
USPC ................................................ 131/352, 347
See application file for complete search history.

(56) References Cited

U.S. PATENT DOCUMENTS

| | | | |
|---|---|---|---|
| 1,492,600 A | 5/1924 | Laskey | |
| 2,433,877 A | 1/1948 | Wells et al. | 131/15 |
| 3,411,515 A | 11/1968 | Hind et al. | 131/140 |
| 3,693,629 A | 9/1972 | Broughton | 131/5 |
| 4,136,162 A | 1/1979 | Fuchs et al. | 424/27 |
| 4,144,894 A | 3/1979 | Schmidt et al. | 131/17 AC |
| 4,581,232 A | 4/1986 | Peters et al. | 424/155 |
| 4,606,357 A | 8/1986 | Dusek et al. | 131/359 |
| 4,624,269 A | 11/1986 | Story et al. | 131/352 |
| 4,625,737 A | 12/1986 | Keritsis et al. | 131/355 |
| 4,650,663 A | 3/1987 | Peters et al. | 424/484 |
| 4,849,246 A | 7/1989 | Schmidt | 427/2 |
| 4,855,326 A | 8/1989 | Fuisz | 514/777 |
| RE33,093 E | 10/1989 | Schiraldi et al. | 424/676 |
| 5,097,851 A | 3/1992 | Ehling et al. | 131/375 |
| 5,948,430 A | 9/1999 | Zerbe et al. | 424/435 |
| 6,072,100 A | 6/2000 | Mooney et al. | 602/48 |
| 6,375,963 B1 | 4/2002 | Repka et al. | 424/402 |
| 6,596,298 B2 | 7/2003 | Leung et al. | 424/435 |
| 6,669,839 B2 | 12/2003 | Tipton et al. | 210/85 |
| 6,834,654 B2 | 12/2004 | Williams | 131/352 |
| 6,845,777 B2 | 1/2005 | Pera | 131/270 |
| 6,923,981 B2 | 8/2005 | Leung et al. | 424/439 |
| 7,067,116 B1 | 6/2006 | Bess et al. | 424/78.1 |
| 7,357,891 B2 | 4/2008 | Yang et al. | 264/211.12 |
| 7,425,292 B2 | 9/2008 | Yang et al. | 264/172.19 |
| 2001/0006677 A1 | 7/2001 | McGinity et al. | 424/449 |
| 2002/0168398 A1 | 11/2002 | Delmotte | 424/443 |
| 2003/0107149 A1 | 6/2003 | Yang et al. | 264/134 |
| 2005/0037055 A1 | 2/2005 | Yang et al. | 424/443 |
| 2005/0171083 A1 | 8/2005 | Magnusson et al. | 514/210.17 |
| 2005/0244521 A1 | 11/2005 | Strickland et al. | 424/751 |
| 2006/0207721 A1 | 9/2006 | Slominski et al. | 156/326 |
| 2006/0257463 A1 | 11/2006 | Elsohly et al. | 424/449 |
| 2007/0202057 A1 | 8/2007 | Fankhauser et al. | 424/48 |
| 2007/0207186 A1 | 9/2007 | Scanlon et al. | 424/424 |
| 2008/0029117 A1 | 2/2008 | Mua et al. | 131/352 |
| 2008/0075825 A1 | 3/2008 | Fuisz et al. | 426/534 |

FOREIGN PATENT DOCUMENTS

| | | | | |
|---|---|---|---|---|
| CN | 1354656 A | 6/2002 | | |
| CN | 1822819 A | 8/2006 | | |
| WO | WO 00/42992 | 7/2000 | | |
| WO | WO 03/039518 A1 | 5/2003 | | |
| WO | 2005/004363 | 1/2005 | ............. | H04J 14/06 |
| WO | 2007/138484 | 12/2007 | ............. | A24B 15/16 |

OTHER PUBLICATIONS

Chinese Office Action of Appln. 200880118176 dated Jul. 25, 2011 in English.
International Search Report and Written Opinion, Application No. PCT/US08/11634, 18 pages, Feb. 25, 2009.
John J. Watson; "History: Watson Inc."; www.watson-inc.com; pp. 2, Apr. 23, 2010.
Lunell et al.; "Steady-state nicotine plasma levels following use of four different types of Swedish snus compared with 2-mg Nicorette chewing gum: a crossover study"; Nicotine & Tobacco Research, vol. 7, No. 3; pp. 397-403, Jun. 2005.
International Search Report and Written Opinion, Application No. PCT/US08/11374, 15 pages, Feb. 3, 2009.
Swedish Match; "Nicotine Uptake: Nicotine Uptake from Snus"; www.swedishmatch.com; pp. 4, Apr. 27, 2010.
Ethical Guidelines for Biomedical Research on Human Participants; Edited by: Director-General, Indian Council of Medical Research; New Dehli; pp. 120, Oct. 2006.

(Continued)

*Primary Examiner* — Richard Crispino
*Assistant Examiner* — Dionne Walls Mayes
(74) *Attorney, Agent, or Firm* — Antonelli, Terry, Stout & Kraus, LLP.

(57) ABSTRACT

A nonaqueous, extrudable composition includes at least one thermoplastic polymer in an amount of more than 20 wt % of the whole composition and tobacco. An extruded bioactive product in the form of a sheet can be made by extruding or hot melt shaping a nonaqueous composition comprising at least one thermoplastic polymer and a bioactive agent, the sheet being soluble in a user's mouth and resulting in sustained release of bioactive to the user. The sheet can be in a form that may be placed in contact with the mucosa of the user, and have an average dissolution time of 5 to 50 minutes for delivering the bioactive to the user.

20 Claims, 8 Drawing Sheets

(56) References Cited

OTHER PUBLICATIONS

FDA; "Draft Guidance—Guidance for Clinical Investigators, Sponsors, and IRBs"; Adverse Event Reporting—Improving Human Subject Protection; www.fda.gov/cder/guidance/index.htm; pp. 11, Apr. 2007.

Repka et al.; "Influence of Vitamin E TPGS on the properties of hydrophilic films produced by hot-melt extrusion"; International Journal of Pharmaceutics 202; pp. 63-70, 2000.

Foulds et al.; "Is low-nicotine Marlboro snus really snus"; Harm Reduction Journal 5:9; pp. 5, Feb. 27, 2008.

World Medical Association Declaration of Helsinki; "Ethical Principles for Medical Research Involving Human Subjects"; WMA General Assembly, Tokyo 2004; pp. 5, 2004.

Rodu et al.; "Smokeless Tobacco and Oral Cancer: A Review of the Risks and Detriments"; Critical Reviews in Oral Biology & Medicine, 15:252; http://cro.sagepub.com; pp. 13, 2004.

"Pharmaceutical Extrusion Technology"; edited by Isaac Ghebre-Sellassie and Charles Martin; pp. 410, 2007.

International Preliminary Report on Patentability; PCT/US2008/011634; pp. 15, Apr. 22, 2010.

International Preliminary Report on Patentability; PCT/US2008/011374; pp. 13, Apr. 22, 2010.

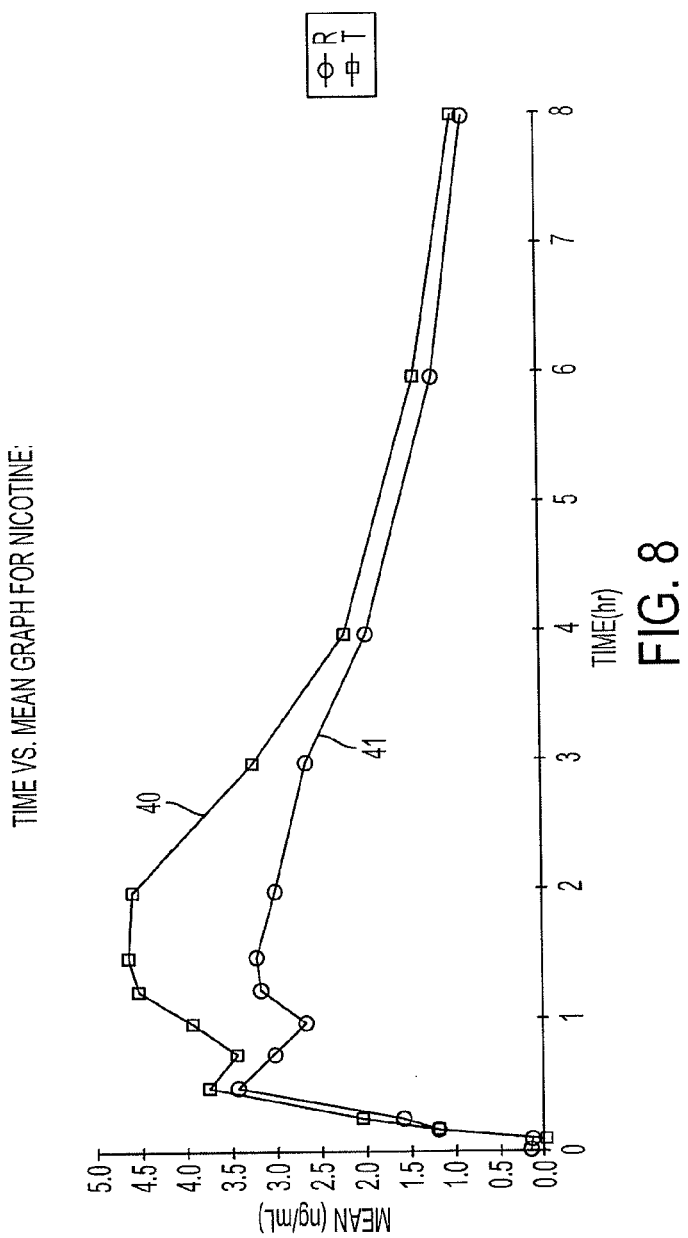

EXTRUDABLE AND EXTRUDED COMPOSITIONS FOR DELIVERY OF BIOACTIVE AGENTS, METHOD OF MAKING SAME AND METHOD OF USING SAME

CROSS REFERENCE TO RELATED APPLICATIONS

This application is a Continuation of U.S. patent application Ser. No. 12/122,201 filed May 16, 2008; and is also a Continuation of International Application No. PCT/US2008/011634 filed Oct. 10, 2008, which designates the United States of America, and claims the benefit of U.S. Provisional Patent Application No. 60/979,169 filed Oct. 11, 2007; U.S. Provisional Patent Application No. 60/990,381 filed Nov. 27, 2007; U.S. Provisional Application No. 61/054,195 filed May 19, 2008, and International Application No. PCT/US2008/011374 filed Oct. 2, 2008. The contents of which are hereby incorporated herein in their entirety by this reference.

BACKGROUND OF THE INVENTION

The present invention relates, inter alia, to a bioactive product, an extrudable bioactive composition, a method for manufacturing a bioactive product and a method for delivering the bioactive contained in the product to a user. The bioactive agent may be, but is not limited to, a pharmaceutical.

The history of solid pharmaceutical dosage forms is straightforward. It began with bioactive powders and these evolved into pressed tablets. Pressed tablet led to capsules and caplets and eventually variants of these evolved which led to liquid core gels etc. Sustained release tablets, such as the osmotic pump system developed by Dr. Zaffaroni at Alza, followed and allowed for sustained release in the GI tract. The next advance was the orally dissolving tablet (ODT) which has been employed to ease dose administration for patients who have difficulty swallowing conventional tablets and capsules, as well as ODT based buccal delivery products such as Cephalon's Fentora®—an ODT system used to administer fentanyl buccally. Various novel methods of manufacturing such ODTs where taught, such as lyophilized quick dissolve forms (ZYDIS®), effervescent quick dissolve systems (CIMA) and ODTs based on a spun sugar matrix (invented by the present inventor, see e.g. U.S. Pat. No. 4,855,326). Copycat, inferior ODT products were then sold, largely based on using tableting processes at low dyne pressure, leading to proposed FDA rule codification to ensure that ODT products actually dissolve quickly (see FDA Draft Guidance dated April 2007 at http://www.fda.gov/CDER/guidance/5909dft.htm).

The next evolution was quick dissolve thin film (partly invented by the present inventor). Thin films are typically made using wet casting manufacturing process and were definitely film as they could only be up to a maximum of 10 mils thick, it being commonly understood that matrix like products become "sheets" when they exceed a thickness of 10 mils. Wet cast film manufacture and products are described in recently granted U.S. Pat. No. 7,425,292 invented by the present inventor: "The films may initially have a thickness of about 500 μm to about 1,500 μm, or about 20 mils to about 60 mils, and when dried have a thickness from about 3 μm to about 250 μm, or about 0.1 mils to about 10 mils. Desirably, the dried films will have a thickness of about 2 mils to about 8 mils, and more desirably, from about 3 mils to about 6 mils." See also U.S. Pat. No. 5,948,430, disclosing wet cast thin film compositions, and stating that "the thickness of films should not exceed 2.7 mils so as to prevent adverse mouth feel." The thickness of commercially available wet cast pharmaceutical film products was measured and found to range from 3 mils—GSK's Breath Right Snore Relief identified as made by MonoSol Rx; 4 mils—Fleet's Pedialax® senna product identified as made by MonoSol Rx, and 6 mils—Novartis' Triaminc® detromethorphan 7.5 mgs which is understood to be manufactured for Novartis by Adhesives Labs of Glen Rock, Pa.

Limitations on wet cast film thickness reflect in part the need to dry the highly aqueous film compositions which gave a practical limitation to the thickness of these films, as well as difficulties in achieving certain wet thicknesses in the coating process itself, discussed herein and related to the challenge of casting the higher molecular weight polymers associated with sufficient viscosity to achieve higher coating thicknesses. Water also serves to lower viscosity. The wet casting process cannot practically deal with very high viscosities as such viscosities cannot be reliably cast using known casting systems. Such limitations point to the utility of the new inventive steps that are shown in this application.

Thickness limitations associated with wet cast films tend to limit loading due to the lack of load carrying ability of the resulting dosage form. This was especially true if taste masking was needed (of course, many high value drug targets still fit within the loading capabilities of wet cast films). Thickness limitations also enable that films are fast dissolving. For example, MonoSol Rx states on its website that it "[specializes in] quick dissolving thin film pharmaceutical products" and further stated in its registration statement with the Securities and Exchange Commission on Form S-1 that "compared to quick-dissolve tablet technologies, our strips disintegrate faster." Other companies with wet cast film making competencies, such as Adhesives Research, Lohmann Therapeutic Systems, Applied Pharmaceutical Research of Switzerland, Labtec of Germany, and Lavipharm of Greece describe their products and technologies in similar terms.

As noted above, edible films are typically made using a wet casting process. In discussing this art, applicant pointedly uses the term "sheet and not "film". This is because the inherent properties of the wet casting manufacturing process—as currently understood—do not allow for the manufacture of thicker sheets (we also refer to "sheets" by a proprietary term "slabs"). Thickness can often relate to dissolution time especially if certain formulae are used. Wet cast edible films are typically quickly dissolving products, and practitioners have struggled—without success—to extend the disintegration time of wet cast edible thin film products where a slower dissolving product would be more appropriate for the intended use. One of the principle problems is that polymer molecular weight is frequently in a direct relationship to viscosity and wet casting is unable to deal with high viscosities.

The development of wet cast edible packaging films for various food and other applications commenced at least fifty years ago (see http://www.watson-inc.com/about_history.php). Other historical antecedents can be seen the wet cast manufacture of fruit pulps as well as rice based films in Asia.

Wet cast monolayer film compositions for pharmaceutical and vitamin delivery are disclosed in Fuchs et al. U.S. Pat. No. 4,136,162 issued Jan. 23, 1979. Schmidt discloses bilayer film compositions for pharmaceutical and food uses in U.S. Pat. No. 4,849,246 issued Jul. 18, 1989.

The inventor Horst Zerbe was issued U.S. Pat. No. 5,948,430 for film compositions for therapeutic agents and breath freshening agents. Zerbe notes, the thickness of films should not exceed 2.7 mils so as to prevent adverse mouth feel. The assignee of this patent, Lohmann Therapeutic Systems ("LTS"), is credited with the manufacture of the first edible film to enjoy commercial succeed—namely, the 2001 commercial launch of pullulan based Listerine PocketPaks® Breath Strips (a product described more fully in Leung et al. 6596298 "Fast dissolving orally consumable films" and Leung et al. 6923981).

The Listerine PocketPaks® film is a very rapidly dissolving film. It dissolves in fewer than ten seconds and has a weight of just 33 mg. The product contains high moisture content and uses water to help impart the product with flexibility (a trait easily demonstrated by drying a Listerine strip—at which point it becomes very brittle and will crack and break when bent).

From breath freshening, wet cast film technology has moved to over-the-counter pharmaceutical products. The emphasis has still been on achieving rapid disintegration in the mouth. Noted thin film drug delivery company MonoSol Rx LLC describes its film technology on its website thusly: "MonoSol Rx has developed a thin film drug delivery technology that is more stable, durable and quicker dissolving than other conventional dosage forms. The thin film, which is similar in size, shape and thickness to a postage stamp, has the ability to carry very low doses of prescription products that are highly uniform, to larger doses up to 80 mg. [italics added]." Those schooled in the art will understand that certain loading achievements are sui generis. The highest loading of a commercial thin film product for a "conventional" active ingredient is Bendadryl®'s 25 mg of diphenhydramine. Novartis also markets a 62.5 mg simethicone product under the Gas-X® brand but such loading is attributable to the unique characteristics of simethicone.

Other pharmaceutical thin film developers, such as LTS, Labtec, Adhesives Research, Lavipharm and Applied Pharma Research describe their film technologies in similar ways. It should be noted that these descriptions of the wet cast products do not address whether the active material is water soluble or insoluble and whether it requires taste masking or does not require taste masking. These factors can have a major effect on loading of the active ingredient as stated above.

The transition of thin film drug delivery into pharmaceutical products required a new focus on meeting pharmaceutical criteria, like achieving and maintaining content uniformity of drug during the wet cast manufacturing process. Wet cast compositional film art developed that could load increasing amounts of drug with continuing emphasis on quick disintegration of the film (see e.g. Yang et al. U.S. Pat. Nos. 7,357,891 and 7,425,292 both of which include the current inventor).

One limitation of wet cast technology is the difficulty—indeed, the inability to wet cast films beyond a certain thickness (or loading) range. This is due to the relationship between viscosity and coating thickness and drying, which creates a practical limitation on the ability to coat beyond certain thickness levels, and the difficulty removing moisture from films past a certain thickness levels, even if they are successfully cast.

Limitations on thickness translate into limits on the amount of bioactive ingredient a film can carry as well as whether absorption modifiers such as ion exchange resins can be carried. As noted above, the largest amount of solid active delivered by a commercially available film is 25 mg of diphenhydramine in Pfizer's fast dissolving Benadryl® strip. Likewise, limitations on thickness also limit the extension of dissolution time of the film matrix. The challenge of extending dissolution times in monolayer wet cast media is evident in Fankhauser et al US 2007/0202057 A1, a case directed at wet cast films containing the drug nicotine. This case uses bench scale formulation tricks including an ice water bath (to gel the polymer) to coax a monolayer wet cast film to a claimed fifteen minute disintegration time. That such a practice would involve immense challenges—arguably impossible—to scale to commercial manufacture is readily apparent.

Others have suggested the lamination of multiple cast films to slow the dissolution of the dosage form (see, e.g. LTS's website). This method is undoubtedly more practical from a manufacturing perspective than Fankhauser's proposed solution, but too costly to practice—particularly in the pharmaceutical space. Thus it is not surprising that such multiple film laminates are not yet seen in the marketplace as commercial products.

Even monolayer wet casting can be relatively expensive. Commercial equipment involves long drying ovens and is too heavy to be moved, requiring specialized and dedicated production suites. Drying requires substantial volumes of filtered air requiring specialized utilities, and substantial amounts of heat energy to remove moisture. With increasing energy costs this is of growing importance in aqueous cast film.

Two additional points must be made—namely, the physical strength and physical stability of wet cast films. Wet cast films are typically cast on a substrate or backing paper. Among other things, the substrate lends physical strength to the film in processing until the film is delaminated from the substrate. However additional costs and process steps to include the use of a substrate backing are involved. Also, the backing can be problematic in terms of the uniform distribution of the cast material on the substrate.

If such films lack the requisite pliability and tensile strength, they will tend to break during packaging causing substantial losses in process yield. Such breakage issues presumably led to the filing of a patent on methods of film splicing by Novartis (Slominski et al US 20060207721 A1). MonoSol Rx makes the most pliable, strong wet cast films, using their polyethylene oxide (PEO) based compositions (See Yang et al. US 2005/0037055 A1). The strength of these films has led to the subsequent use of PEO in formulations commercially sold by Novartis. The reality is that physical strength and resulting breakage and process yield issues have been significant problems for many of the non-PEO wet cast films.

Drying wet cast films requires exacting direction of the drying air in order to avoid surface skin formation and yet requires sufficient flow of hot air to dry off the water content. However, here too, in aqueous wet cast film, the air can be principally directed to the top or bottom of the drying film consistent with the flow patterns permitted in modern dryers (see U.S. Pat. No. 7,425,292).

The related issue of physical stability is also an issue for many wet cast films—expensive barrier packaging is often used as a matter of necessity. Still, physical stability is not always a given. Boots Chemists launched a Vitamin C strip manufactured by BioProgress in Tampa Fla. that had to be removed from the shelves because it was crumbling in the package—earning the name "chips not strips." This story is not unique—many projects have failed to move out from development to commercialization due to physical stability issues.

In addition, the mixing of wet based compositions for casting itself raises certain challenges. First, the solvent itself adds volume to the mix. Wet compositions may tend to adhere to mixing vessels and any transit piping leading to yield losses. They can also involve complex fluidic issues in transit to the casting head.

Foaming may be in issue. Wet mixtures must be de-gassed to avoid air bubbles which can reduce content uniformity. Furthermore, cast aqueous film mixtures may tend to aerate when the aqueous mixture is formed through the mixing process. This then requires deaeration so as not to interfere with uniformity. The deaeration of cast film involves the pulling of vacuum over the wet mixture and the inclusion of various types of deaerators like simethicone etc. Simply put, in cast film, mixing may introduce air in the aqueous mix in cast film and vacuum and deaerating agents may be used to remove it and preserve uniformity. See, Fuisz et al. US 20080075825 A1. In our extruded, non aqueous film this hazard is not present.

Many of the above observations concerning aqueous wet casting apply equally to wet casting that employs non-water solvents.

Extruded edible products have a lengthy history—confections were being extruded in the 1920's (See P. B. Laskey U.S. Pat. No. 1,492,600). Extrusion has more recently been used in medical device manufacture and in the making of transdermal drug delivery systems—of course, these are both non-edible and insoluble. See, generally, *Pharmaceutical Extrusion Technology*, edited by Issac Ghebre-Sellassie and Charles Martin (2007), the content of which is incorporated herein in its entirety.

Inspired by the success of transdermal drug delivery systems, work began to extrude soluble, edible sheets and films for drug delivery use.

Schiraldi et al. (U.S. RE33,093) discloses bioadhesive monolayer extruded films, under 10 mils, composed of principally of polyethylene oxide together with a lesser amount of HPC, a water insoluble polymer; a plasticizer and a medicament. See also Mooney and Schiraldi, U.S. Pat. No. 6,072,100 disclosing compositions extruded films and sheets comprising a composition of PEO or HPC, a water polymer derived from a carboxylic aid, 30-80% plasticizer and up to 10% of a medicament.

Michael Repka and James McGinnity disclose hot melt extruded sheets with a thickness of 10-13 mils using a 50-50 ratio PEO and HPC, together with 3% of Vitamin E TPGS (see "Influence of Vitamin E TPGS on the properties of hydrophilic films produced by hot melt extrusion," International Journal of Pharmaceutics 202 (2000) 63-70).

Repka et al U.S. Pat. No. 6,375,963 issued Apr. 23, 2002 disclose a hot-melt extruded film and method of preparation thereof. The inventors note that "[f]ilms comprising pure hydroxypropylcellulose (HPC) and other water-soluble or water-swellable polymers cannot be readily produced by hot-melt extrusion due to the high stress that is exhibited on the extruder. Therefore plasticizers have been added to the HPC and other polymers" and that "the prior art does not disclose that films comprising a major portion of HPC and other water-soluble or water-swellable polymers can be produced by hot-melt extrusion in the absence of a plasticizer." To solve this problem Repka et al propose using a bioadhesive polymer instead of a plasticizer. The film of Repka et al is made from a precursor composition containing at least a water soluble or water swellable thermoplastic polymer, preferably HPC and/or PEO, and a bioadhesive polymer. The film can also contain a therapeutic agent, preservative, buffering agent, antioxidant, super-disintegrant or absorbent, flavorant, colorant, water insoluble polymer, organic acid, surfactant, film modifier, and/or cross-linking agent. The film does not contain a conventional plasticizer or a material which is generally recognized in the art as a plasticizer for extruded films. Repka et al claim, inter alia, a hot-melt extruded film including one or more water-soluble or water-swellable thermoplastic polymer or polymers, a therapeutic agent; and a bioadhesive polymer. The bioadhesive polymer is selected from the group consisting of polycarbophil, carbomer, one or more acrylic polymers, one or more polyacrylic acids, copolymers of these polymers, a water soluble salt of a co-polymer of methyl vinyl ether and maleic acid or anhydride, a combination thereof and their salts.

A review of the Orange Book indicates that none of the above extrusion patents are used in an FDA approved pharmaceutical product nor are any such patents referenced on any over-the-counter product.

As the art demonstrates, practitioners have struggled to achieve required flexibility in hot melt extruded pharmaceutical films, and have relied on PEO, polycarbophil or extreme levels of plasticizer to achieve such flexibility of the sheet or film. Neither PEO nor polycarbophil is approved for food use outside of the US. Additionally, PEO is a very expensive polymer that is ill suited from a cost perspective and may tend to dissolve too quickly for many applications. As a result, the pharmaceutical art on extruded films and sheets provides little guidance for the composition of the present invention.

As is seen the pharmaceutical art concerning hot melt extrusion of sheets and/or films containing active ingredients involves real challenges which must be overcome, as they are by the present invention.

Thus, it is still desirable to provide a more efficient way to produce a bioactive containing sheet so as to allow the absorption of the bioactive agent. This is accomplished using a slab or sheet dosage form as put forth below.

BRIEF SUMMARY OF THE INVENTION

The present invention relates to a nonaqueous, extrudable composition comprising at least one thermoplastic polymer in an amount of more than 20 wt % of the whole composition and a bioactive agent.

The present invention also relates to a pharmaceutical product comprising a sheet made by extruding or hot melt shaping a nonaqueous composition comprising at least one thermoplastic polymer and one or more bioactive ingredients, the sheet comprising a matrix comprising the at least one thermoplastic polymer and one or more bioactive ingredient(s) distributed in the matrix, the matrix being soluble in a user's mouth and resulting in sustained release of the bioactive to the user.

The present invention also relates to a pharmaceutical product comprising a non aqueous composition comprising at least one thermoplastic polymer and one or more bioactive ingredients in a form that may be placed on any of the mucosa, e.g., oral (buccal, gingival, sublingual or palatal), nasal, rectal or vaginal of a user and having an average dissolution time of 5 to 50 minutes, measured for a composition in the form of a sheet having a surface area of approximately 0.25-1.5 in$^2$ and a thickness of approximately 10-70 mil, to dissolve fully.

The present invention also relates to a pharmaceutical product comprising a matrix with one or more bioactive ingredients in an amount of less than 1000 mg, preferably less than 500 mg, more preferably less than 300 mg. The present invention also relates to a method for making a pharmaceutical product, comprising extruding a nonaqueous composition comprising at least one thermoplastic polymer in an amount of more than 20 wt % the whole composition and one or more bioactive ingredients through an extruder to form an extruded slab or sheet of the nonaqueous composition.

The present invention also relates to a method for delivering super bioavailable bioactives from a pharmaceutical product containing one or more bioactives to a user, comprising providing a sheet comprising an extruded nonaqueous composition comprising at least one thermoplastic polymer and such bioactive ingredient(s); and placing the sheet in the buccal mucosa of, or on the palate of or sublingual mucosa in the oral cavity of the user.

The present invention also relates to a method for delivering super Bioavailable bioactives from a pharmaceutical product containing one or more bioactives to a user, comprising providing a sheet comprising an extruded nonaqueous composition comprising at least one thermoplastic polymer and ion exchange resins in conjunction with bioactive ingredient(s); and placing the sheet on any of the mucosa, e.g., oral (buccal, gingival, sublingual or palatal), nasal, rectal or vaginal or on or in a wound of the user.

BRIEF DESCRIPTION OF THE DRAWINGS

FIG. 8 is nicotine plasma concentration time curve vs. time comparing a sheet containing nicotine naturally occurring in tobacco according to the present invention against a 2 mg gum, according to Example Q.

DETAILED DESCRIPTION OF THE INVENTION

Figure 1:
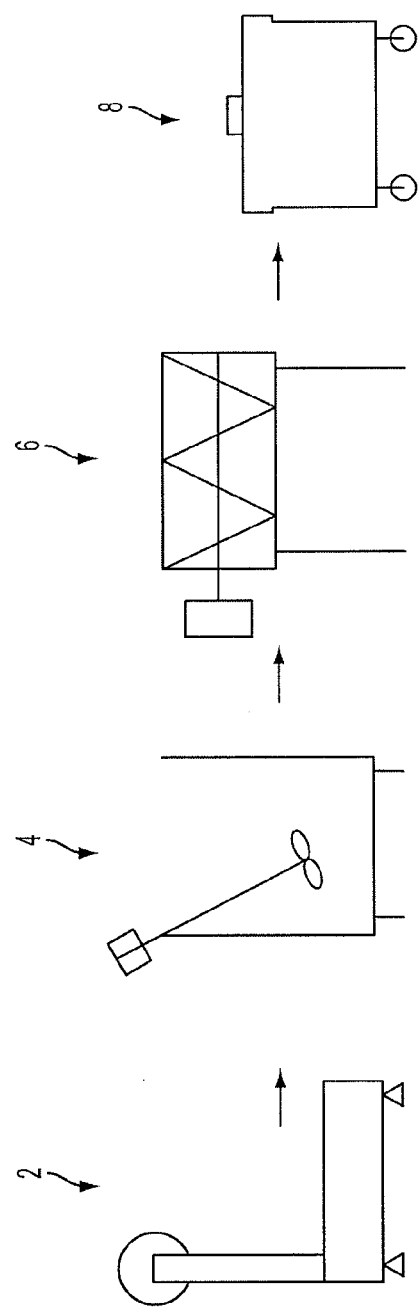
FIG. 1 is a schematic diagram showing one example of a mixing process that can be used in the manufacturing method for the pharmaceutical product of the present invention.

In one aspect of the present invention, the invention relates to a nonaqueous, extrudable composition comprising at least one thermoplastic polymer and one or more bioactive ingredients.

Applicant has found unexpectedly that, contrary to the indication in the aforementioned Repka et al patent, a nonaqueous composition comprising at least one thermoplastic polymer in an amount of more than 20 wt % of the whole composition and a bioactive agent can be readily extruded to form a sheet, even though the composition does not necessarily contain PEO, polycarbophil or other bioadhesive material (polycarbophil, carbomer, one or more acrylic polymers, one or more polyacrylic acids, copolymers of these polymers, a water soluble salt of a co-polymer of methyl vinyl ether and maleic acid or anhydride, a combination thereof and their salts), or plasticizers.

By the term "nonaqueous," applicants mean that the composition includes a number of materials but that no water or other aqueous solvent has been added in addition to any water, moisture or aqueous solvent that may be present in the other materials in the composition. For example, the composition may contain a bioactive ingredient that may have a small amount of residual moisture content and/or a flavoring that may itself be aqueous, but the composition does not contain any water in addition to the residual moisture content in the bioactive ingredient and/or any water in the flavoring; therefore, such a composition would still be considered "nonaqueous" as that term is defined herein. Preferably, the nonaqueous composition of the present invention contains less than 20 wt %, more preferably less than 12.5 wt %, and more preferably less than 10 wt % water prior to extrusion, preferably less than 6 wt %, and more preferably less than 4 wt % water after extrusion or hot melting. Thermoplastic polymer, polymer and matrix formers that are thermo-processable are preferred. The thermoplastic polymer may comprise at least one polymer selected from the group consisting of cellulose ethers, polyethylene oxide, polymethacrylates, poloxamers, extrudable carbohydrates, polyethylene glycols (PEG), PVP, poly vinyl alcohol, acrylates, ethyl cellulose, cellulose acetate butyrate, copolymers such as poly(ethylene-co-vinyl acetate) copolymer and poly(methylvinyl ether/maleic anhydride) co-polymer, poly vinyl acetate, pullulan, hydroxypropyl cellulose (HPC), hydroxypropyl methylcellulose (HPMC), amorphous polysaccharides and polycarbophyl. Preferably, the thermoplastic polymer is water soluble.

In one embodiment of the invention, a cellulose ether such as hydroxypropyl cellulose (HPC) is preferred. Examples of commercially available HPC that can be used include KLUCEL® EF, ELF and LF hydroxypropylcellulose (HPC) sold by Hercules Incorporated, Aqualon Division, of Wilmington, Del. (referred to hereinafter, respectively, as HPCEF, HPCELF and HPCEF).

If PEO is used, it is preferred that the molecular weight of the PEO is 100,000 or greater and less than 1,000,000. The PEO can also be used in combination with other polymers. If PEO is used, it is preferred that Vitamin E and Vitamin E derivatives be used as a stress crack eliminator. 1 to 15% of Vitamin E or Vitamin E derivative functions to eliminate such stress cracking with 5 to 10% preferred and 5% most preferred.

Certain insoluble polymers may be used in conjunction with insoluble polymers to extend the dissolution time. They may sometimes be present in the ion exchange resins/drug combinations. Particle size is desirable to be less than 500 microns, preferably less than 200 microns and most preferably less than 150 microns.

The nonaqueous, extrudable composition comprises at least one such thermoplastic polymer in an amount of more than 20 wt % of the whole composition. Preferably, the composition comprises at least one such thermoplastic polymer in an amount less than 50 wt %, more preferably less than 40 wt %, and most preferably less than 30% of the weight of the whole composition.

The bioactive agent of the present invention is preferably a pharmaceutical but may be any biological, antigen, botanical, food or nutraceutical, cosmaceutical or other active agent.

Examples of pharmaceutical bioactive agents include, but are not limited to ace inhibitors, such as Benazepril, Captopril, Enalapril, Lisinopril, Moexipril, Perindopril, Quinapril, Ramipril and Trandolapril; acne treatments, such as adapalene, azelaic acid, BenzaClin, Benzamycin, Benzoyl Peroxide, clindamycin, Duac, Erythromycin, Glycolic Acid, Isotretinoin, Sulfacetamide with sulfur, Tazarotene and Tretinoin; actinic keratosis, such as declofenac, fluorouracil; addiction aids, such as buprenorphine, Disulfuram, Naltrexone, Suboxone and varenicline; aldosterone antagonists, such as eplerenone and spironolactone; alpha-1 adrenergic blockers, such as alfuzosin, doxazosin, prazosin, tamsulosin and terazosin; ALS agents, such as riluzole; Alzheimer's Disease medications, such as donepezil, Galantamine, rivastigmine, tacrine and memantine; anesthetics, such as dexmedetomidine, etomidate, ketamine, methohexital, pentobarbital, propofol and thiopental; angiotensin II receptor blockers, such as candesartan, eprosartan mesylate, irbesartan, losartan, olmesartan, telmisartan and valsartan; antacids, such as Aluminum hydroxide, AlOH and magnesium trisilicate; anti-arrhythmics, such as adenosine, amiodarone, Atropine, Bretylium, digoxin-Immune Fab, disopyramide, dofetilide, epinephrine, Esmolol, flecainide, ibutilide, isoproterenol, lidocaine, mexiletine, moricizine, procainamide, propafenone, quinidine, sotalol, tocainide and verapamil; antibiotics, such as Aztreonam, TMP/SMX, Chloramphenicol, Clindamycin, Dapsone, Daptomycin, Ertapenem, Imipenem/cilastatin, Linezolid, Meropenem, Metronidazole, Nitrofurantoin, Quinupristin/Dalfopristin, Rifaximin, Tigecycline, Telithromycin and Tinidazole; anticholinergic acids, such as Dicyclomine, Donnatal, Flavoxate, Glycopyrrolate, Hyoscyamine, Oxybutynin, Propantheline and Tolterodine; anti-convulsants, such as carbamazepine, clonazepam, diazepam, ethosuximide, felbamate, fosphenytoin, gabapentin, levetiracetam, lamotrigine, lorazepam, Oxcarbazepine, Phenobarbital, phenyloin, pregabalin, primidone, tiagabine, topiramate and valproic acid; antidepressants, such as amitriptyline, buprorion, citalopram, desipramine, doxepin, duloxetine, escitalopram, fluoxetine, fluvoxamine, imipramine, mirtazapine, nefazodone, nortriptyline, nortriptyline, sertraline, trazodone and venlafaxine; anti-diarrheals, such as dephenoxylate+atropine, Imodium and bismuth subsalicylate; anti-emetics, such as Aprepitant, dolasetron, droperidol, granisetron, metoclopramide, ondansetron, prochlorperazine, scopolamine and trimethobenzamide; antifungals, such as Ampho B, Ampho B lipid, anidulafungin, caspofungin, Clotrimazole fluconazole, flucytosine, Griseofulvin, Itraconazole, ketoconazole, Micafungin, nystatin, Posaconazole, terbinafine, voriconazole, butenafine, ciclopirox, clotrimazole, enconazole, ketoconazole, Miconazole, naftifine, nystatin, oxiconazole terbinafine and Tolnaftate; anti-hepatitis, such as adefovir, entecavir, lamivudine, peginterferon aifa-2a, peginterferon aifa-2b, Rebetron and ribavirin; anti-herpetic agents, such as Acyclovir, famciclovir, valacyclovir, acyclovir, docosanol and penciclovir; antihistamines, such as cetirizine, desloratadine, fexofenadine, loratadine, chiorpheniramine, ciemastine, cyproheptadine, dimenhydrinate, diphenhydramine, hydroxzine and promethazine; anti-hypertension, such as Benazepril & HCTZ, Captopril & HCTZ, Enalapril & HCTZ, Lisinopril & HCTZ, Moexipril & HCTZ, Losartan & HCTZ, Vaisartan & HCTZ, Atenolol & chiorthalidone, Bisoprolol & HCTZ, Metoprolol & HCTZ, Nadolo! & bendrofiumethazide, Propranolol & HCTZ, Timolol & HCTZ, Amlodipine & benazepril, Verapamil & trandolapril, Amiloride & HCTZ, Spironolactone & HCTZ, Triamterene & HCTZ, Clonidine & chiorthalidone, Hydralazine & HCTZ, Methyldopa & HCTZ and Prazosin & polythiazide; antihypertensives, such as Aliskiren, Aliskiren, epoprostenol, fenoldopam, hydralazine, minoxidil, nitroprusside, phentolamine and treprostinil; anti-influenza agents, such as amantadine, oseltamivir phosphate, rimantadine and zanamivir; antimalarials/anti-protozoals/amebicides, such as Atovaquone, Chloroquine, Iodoquinol, Mefloquine, Primaquine, Pyrimethamine, Pyrimethamine-Suifadoxine and Quinine Sulfate; anti-platelet agents, such as abciximab, dipyridamole/ASA, anagrelide, cilostazol, clopidogrel, dipyridamole, eptifabatide, ticlopidine and tirofiban; antipsychotics, such as aripiprazole, chlorpromazine, Clozapine, fluphenazine, haloperidol, loxapine, molindone, olanzepine, perphenazine, pimozide, quetiapine, risperidone, thioridazine, thiothixine, trifluoperazine, ziprasidone and Lithium; antispasmotics, such as Dicyclomine, Donnatal Extentabs, Propantheline, Simethicone, hyoscyamine, Librax, tegaserod and Bellergal-S; anti-tussives/expectorants, such as Benzonatate and guaifenesin; atopic dermatitis medications, such as pimecrolimus and tacrolimus; benzodiazepines and non-benzodiazepine sedatives, such as aiprazolam, buspirone, chlordiazepoxide, chlorazepate, cionazepam, diazepam, estazolam, eszcpiclone, flurazepam, lorazepam, midazolam, Oxazepam, ramelteon, temazepam, triazolam, zaleplon and zolpidem; beta blockers, such as atenolol, betaxolol, bisoprolol, carvedilol, esmolol, labetalol, metoprolol, nadolol, pindolol, propranolol, sotalol and timolol; bile acid sequestrants, such as cholestyramine, colesevelam and colestipol; bisphosphonates, such as alendronate, etidronate, pamidronate, risedronate, tiludronate and Zoledronic acid, Raloxifene and Teriparatide; bladder spasm medications, such as flavoxate, hyoscyamine, darifenacin, oxybutynin, soiifenacin, tolterodine and trospium; benign prostatic hypertrophy medications, such as alfuzosin, doxazosin, dutasteride, finasteride, tamsulosin and terazosin; burn preparations, such as mafenide acetate and silver sulfadiazine; calcium channel blockers, such as amlodipine, bepridil, diltiazem, felodipine, isradipine, nicardipine, nifedipine and nisoldipine; calcium supplements, such as Calcium and Hypocalcemia; cephalosporins, such as Cefadroxil, Cefazolin, Cephradine, Cephalexin, Cefaclor, Cefotetan, Cefoxitin, Cefprozil, Cefuroxime, Cefuroxime, loracarbef, Cefdinir, Cefixime, Cefoperazone, Cefotaxime, Cefpodoxime, Ceftazidime, Ceftibuten, Ceftizoxime and Cefepime; colony stimulating factors, such as darbepoietin alfa, erythropoietin, filgrastim, oprelvekin, pegfilgrastim and sargramostim; corticosteroids, such as Budesonide, cortisone acetate, dexamethasone, fludrocortisones, hydrocortisone, methylprednisolone and prednisone; corticosteroids Intra-articular, such as Depo-Medrol and Triamcinolone Acetonide; cystitis, such as pentosan polysulfate, Bethanecol and Alum irrigation; decongestants, such as Phenylephrine and Pseudoephedrine; anti-diabetic agents, such as acarbose, Miglitol and metformin, Avandamet®, Glucovance, Metaglip, Metaglip, rosiglitazone, osiglitazone, repaglinide, Chlorpropamide, glimepiride, glyburide, glipizide, Tolazamide, Tolbutamide, Glucagon, extenatide and pramlintide; direct thrombin inhibitors, such as argatroban, Bivalirudin and lepirudin; disease modifying agents, such as adalimumab, anakinra, auranofin, azathioprine, etanercept, hydroxychloroquine, infliximab, leflunomide, methotrexate and sulfasalazine; diuretics, such as Acetazolamide, Amiloride, Amiloride and HCTZ Bendroflumethiazide, Bumetanide, Chlorothiazide, Chlorthalidone, Dichlorphenamide, Eplenerone, Ethacrynic acid, Furosemide, Hydrochlorothiazide, HCTZ rrriampterene, Hydroflumethiazide, Indapamide, Methazolamide, Methyclothiazide, Methyclothiazide, Metolazone, Polythiazide, Spironolactone, Spironolactone, HCTZ Torsemide, Trichlormethiazide and Triamterene; endocrine agents, such as bromoc cinacalcet cosyntropin, riptine, cabergoline, calcitonin, desmopressin, Leuprolide, octreotide and vasopressin; erectile dysfunction agents, such as Sildenafil, tadalafil, vardenafil; fever medications, such as allopurinol, antihistamines, azathioprine, barbiturates, carbamazepine, cephalosporins, cimetidine, folic acid, hydralazine, hydroxyurea, ibuprofen, isoniazid, methyldopa, nitrofurantoin, penicillins, phenyloin, phenyloin, procainamide, prophylthiouracil, quinidine, streptomycin sulfonamides, sulindac, triamterene and vancomycin; fibrates, such as ciofibrate, fenofibrat and gemfibrozil; fluoroquinolones, such as Ciprofloxacin, Gatifloxacin, Levofloxacin, Moxifloxacin, Norfloxacin and Ofloxacin; gastrointestinal agents, such as Alosetron, infliximab, Mesalamine, misoprostol, Neomycin, octreotidev, osaiazine, Orlistat, sucralfate, Sulfasalazine and vasopressin; gout treatments, such as allopurinol, coichicine, probenecid, Rasburicase and sulfinpyrazone; H2 receptor blockers, such as cimetidine, famotidine, nizatidine and ranitidine; Anti-herpetic agents, such as Acyclovir, famciclovir, valacyclovir, acyclovir, docosanol and penciclovir; hypertensive urgency, such as Captopril, Clonidine and Labetalol; hypertensive emergency, such as Enalaprilat, Esmolol, Fenoldopam mesylate, Hydralazine, Labetalol, Nicardipine, Nitroglycerin and Sodium nitroprusside; hemorrhoidal preparations, such as Anusol HC, Anusol Suppository, Dibucaine, pramoxine 1%, Proctofoam-HC and Analpram-HC; inflammatory bowel disease agents, such as balsalazide, budesonide, infliximab, mesalamine, olsalazine and sulfasalazine; Interferon, such as Interferon Alfa-2A, Interferon Alfa-2b, Interferon Alfa-2b and Ribavirin combo Pack, Interferon Alfa-N3, Interferon Beta-1A, Interferon Beta-1B (Betaseron); intermittent claudication, such as ciiostazol and pentoxifylline; immunizations, such as Comvax, diphtheria-tetanus toxoid, Hepatitis A vaccine, Hepatitis B vaccine, Influenza vaccine, Fluzone, Lyme disease vaccine, PNEUMOVAX* 23; laxatives, such as Bisacodyl, Cascara, Docusate, Fleet Phospho-Soda, Glycerin, Lacalutose, lubiprostone, Magnesium citrate, Magnesium hydroxide—MOM, Mineral Oil, Pericolace, Psyllium and Senna; low molecular weight heparins, such as dalteparin, danaparoid, enoxaparin, tinzaparin, fondaparinux; macrolides, such as Azithromycin, Clarithromycin and Erythromycin; magnesium, such as magnesium salt; migraine treatments, such as almotriptan, eletriptan, frovatriptan, naratriptan, rizatriptan, sumatriptan, zolmitriptan, Cafergot®, Cafergot®, dihydroergotamine and Midrin®; mouth and lip treatments, such as amlexanox, Benzocaine, carbamide, peroxide, Kenalog in Orabase®, Phenol, chlorhexidine gluconate, clotrimazole, Nystatin, Penciclovir, docosanol, Gelclair, lidocaine viscous, BMX Cocktail, Pilocarpine and Artificial saliva; multiple sclerosis treatments, such as glatiramer, interferon beta-1A and interferon beta-1 B; muscle relaxants, such as baclofen, carisprodol, cyclobenzaprine, cyclobenzaprine, Diazepam, Metaxalone, Methocarbamol, Orphenadrine; nasal preparations, such as azelastine, beclomethasone, budesonide, cromolyn, desmopressin acetate, fiunisolide, fluticasone, Ipratropium bromide, mometasone, oxymetazoline, phenylephrine, Saline nasal spray, Sumatriptan, triamcinolone and Zolmitriptan; urology treatments, such as Belladonna and opium, flavoxate, hyoscyamine, hyoscyamine, oxybutynin, solifenacin, tolterodine and trospium; neuromuscular blockers, such as Atracurium, Cisatracurium, doxacurium, mivacurium, pancuronium, Rocuronium, Succinylcholine, vecuronium, Mivacurium, Rapacuronium, Rocuronium, Succinylcholine, Atracurium, Cisatracurium, Pancuronium, Vecuronium, Doxacurium, Pipecuronium and Tubocurarine; nitrates, such as Isosorbide dinitrate, Isosorbide mononitrate, Nitroglycerin ointment, Nitrobid and Nitroglycerin transdermal; NSAID's, such as Arthrotec, diclofenac, Etodolac, indomethacin, Ketorolac, Sulindac, Tolmentin Diflunisal Salsalate Meloxicam, piroxicam, Nabumetone Flurbiprofen, Ibuproven, Ketoprofen, Naproxen, Oxaprozin, celecoxib, Rofecoxib and Valdecoxib; ophthalmic agents, such as, proparacaine, tetracaine, Ciprofloxacin, Erythromycin, Gentamcyin, levofloxacin, levofloxacin, norfloxacin, Ofloxacin, Polysporin®, Polytrim, Sulfacetamide, Tobramycin, Blephamide®, Blephamide®, Maxitrol®, Pred G® and TobraDex®, Dexamethasone, Fluorometholone, Loteprednol, Prednisone, Rimexolone, azelastine, Cromolyn sodium, emedastine, Epinastine, Ketotifen Fumarate Ophthalmic Solution 0.025°/o, Levocabastine, Lodoxamide tromethamine, Naphazoline, Naphcon-A®, nedocromil, Olopatadine, pemirolast, Betaxolol, Betaxolol, Levobunolol, TimoloE, Brinzolamide, Dorzolamide, Pilocarpine, bimatoprost, Latanoprost, travoprost, unoprostone, Apraclonidine, Brimonidine, Cosopt® and Cosopt®, Atropine, Cyclopentolate, Homatropine, Phenylephrine, Phenylephrine, Diclofenac, Flurbiprofen and Ketorolac; ear (otic) preparations, such as Auralgan®, carbamide peroxide, CIPRODEX®, Ciprofloxacin and hydrocortisone, Cortisporin®, Ofloxacin, Triethanolamine and Vosol Otic®; opiates, such as Codeine Fentanyl Hydrocodone Hydrocodone, Meperidine Methadone, morhphine, xycodone, Propoxyphene, Darvon®, Fioricet, Fiorinal, Soma compound, Tramadol, Anexsia, Darvocet, Darvon Compound, Lorcet, Lortab, Percocet, Percodan, Roxicet, Tylenol with Codeine, Tylox, Vicodin, Wygesic, Buprenorphene, Butorphanol, Dezocine, Nalbuphine, Pentazocine, Nalmefene Naloxone, Suboxone® and Ziconotide; parkinson's disease treatments, such as amantadine, benztropine, bromocriptine, entacapone, pergolide, pramipexole, ropinirole, selegiline, Sinemet®, tolcapone and trihexyphenidyl; PCA—Patient Controlled Analgesia, such as Fentanyl, Hydromorphone, Meperidine and Morphine; penicillin's, such as Ampicillin, Ampicillin/sulbactam, Amoxicillin, Amoxicillin/Clavulanate, Cloxacillin, Dicloxacillin, Nafcillin, Penicillin G, Penicillin VK, Piperacillin, Piperacillin/Tazobactamm, Ticarcillin, and Ticarcillin/Clavulanate; phosphate supplementation, such as, K-Phos® Neutral Tablets, K-PHOS® ORIGINAL, Neutra-Phos®; potassium supplementation, such as K-LOR, Klor-Con®, Potassium depletion; prostate cancer medications, such as bicalutamide, flutamide, gosereiin, leuprolide and nilutamide; proton pump inhibitor's, such as esomeprazole, Lansoprazole, Omeprazole, Pantoprazole and Rabeprazole Sodium; psoriasis medications, such as acitretin, aiefacept, Anthralin, Caicipotriene, efalizumab and Tazarotene; renal failure medications, such as Aluminum Hydroxide, Calcium acetate, Calcitriol, Doxercalciferol, Ferric Sodium Gluconate, paricalcitol and sevelamer; pulmonary medications, such as ipratropium, tiotropium, albuterol, bitolterol, levalbuterol, pirbuterol, metaproterenol, formoterol, salmeterol, Advair®, Symbicort®, beclomethasone, budesonide, flunisofide, fluticasone, Mometasone furoate, triamcinolone, montelukast Singulair®, zafirlukast, cromolyn sodium, nedocromil, acetylcysteine and aminophylline/theophyliine; disease modifying agents, such as adalimumab, anakinra, auranofin, azathioprine, etanercept, hydroxychloroquine, infliximab, leflunomide, methotrexate and sulfasalazine; HMG COA reductase inhibitors, such as Atorvastatin, Fluvastatin, Lovastatin, Pravastatin, Rosuvastatin, Simvastatin, Advicor®, Vytorin® and ezetimibe; stimulants, such as atomoxetine, benzphetamine, Caffeine, dexmethylphenidate, Dextroamphetamine, diethylpropion, Methylphenidate, Modafinil, Pemoline, phendimetrizine, phentermine and sibutramine; tetracyclines such as Doxycycline, Minocycline and Tetracycline; thrombolytic agents such as Alteplase; anti-thyroid agents such as methimazole and propylthiouracil; toxicology related medications such as acetylcysteine, Charcoal, deferoxamine, digoxin immune fab, flumazenil, fomepizole, methylene blue, naloxone, sodium polystyrene sulfonate and Sorbitol; anti-mycobacterial agents such as Ethambutol, Isoniazid, Pyrazinamide, rifabutin, Rifamate, Rifampin, Rifapentine and Rifater; topical products such as Alitretinoin, Becaplermin, Calamine, Capsaicin, Doxepin, lidocaine/prilocaine, fluorouracil, Masoprocol, Pimecrolimus, Selenium sulfide and Tacrolimus; topical anti-viral agents such as acyclovir, docosanol, imiquimod, penciclovir, podofilox and podophyllin; topical antibacterials such as bacitracin, rnetronidazole, mupirocin, bacitracin/neomycin/polymyxin, bacitracin/polymyxin and silver sulfadiazine; topical antifungals such as butenafine, ciclopirox, clotrimazole, econazole, ketoconazole, miconazole, naftifine, nystatin, oxiconazole, terbinafine and tolnaftate; topical anti-parasitic agents such as Crotamiton, Lindane, Permethrin, pyrethrins and piperonyl butoxide; topical burn preparations such as mafenide acetate and silver suifadiazine; topical corticosteroids such as Aclometasone diproprionate, Desonide, Flucinolone acetonide, Hydrocortisone, Betamethasone dipropionate, betamethasone valerate, clocortolone pivalate, desoximetasone, fluocinolone acetonide, flurandrenolide, fluticasone propionate, Chydrocortisone butyrate, hydrocortisone valerate, mometasone furoate, prednicarbate, triamcinoione, amcinonide, augmented betamethasone dipropionate, betamethasone dipropionate, desoximetasone, diflorasone diacetate, fluocinalone acetonide, fluocinonide, halcinonide, clobetasol propionate, difiorasone diacetate and haiobetasol propionate; urology medications such as pentosan polysulfate, Bethanecol and phenazopyridine; vaginal preparations such as clindamycin, metronidazole, butoconazoie, clotrimazole, miconazoie, terconazole and tioconazole; vasodilators such as Fenoldopam mesylate, Hydralazine, Nesiritide, Nicardipine, Nitroglycerin, and Sodium Nitroprusside; and vasopressors and inotropes such as Dobutamine, Dopamine, Epinephrine, inamrinone, Milrinone, Norepinephrine, Phenylephrine, and Vasopressin.

Examples of food or nutraceutical bioactive agents include, but are not limited to, constituents in foods or dietary supplements that are responsible for changes in health status, such as components of plants, especially fruits and vegetables, e.g., soy which contains isoflavones and phytoestrogens, tomatoes which contain lycopene that may have anti-cancer properties, berries such as blueberries and raspberries which contain flavonoids like anthocyanins that may act as antioxidants, green tea which contains epigallocatechin gallate (EGCG) that may have anticancer properties, resveratrol from red grape products as an antioxidant, soluble dietary fiber products, such as psyllium seed husk for reducing hypercholesterolemia, broccoli (sulforaphane) as a cancer preventative, and soy or clover (isoflavonoids) to improve arterial health. Flavonoids, antioxidants, alpha-linolenic acid from flax seeds, extracts such as ginseng, garlic oil, etc. Examples of biological bioactive agents include, but are not limited to biologically active substances in plants that have proven (e.g. cholesterol lowering effects of phytosterols) or potential beneficial effects on health, i.e., phytochemicals or phytonutrients, in particular phytochemicals in leaves, stems, roots, tubers, buds, fruits, seeds and flowers, and plant derived foods and drinks (such as tea, coffee, alcoholic beverages), such as flavonoids found in a range of plant derived foods including tea, wine, onions, apples and berries, glucosinolates from Cruciferous vegetables, phenolic acids in tea and coffee for example, and carotenoids (some of which are precursors of vitamin A) prevalent in red, green and orange fruits and vegetables.

Examples of antigen bioactive agents include, but are not limited to exogenous antigens, endogenous antigens, autoantigens and tumor antigens. Exogenous antigens are antigens that have entered the body from the outside, for example by inhalation, ingestion, or injection. By endocytosis or phagocytosis, these antigens are taken into the antigen-presenting cells (APCs) and processed into fragments. APCs then present the fragments to T helper cells (CD4$^+$) by the use of class II histocompatibility molecules on their surface. Some T cells are specific for the peptide:MHC complex. They become activated and start to secrete cytokines. Cytokines are substances that can activate cytotoxic T lymphocytes (CTL), antibody-secreting B cells, macrophages, and other particles. Endogenous antigens are antigens that have been generated within the cell, as a result of normal cell metabolism, or because of viral or intracellular bacterial infection. The fragments are then presented on the cell surface in the complex with MHC class I molecules. If activated cytotoxic CD8+ T cells recognize them, the T cells begin to secrete various toxins that cause the lysis or apoptosis of the infected cell. In order to keep the cytotoxic cells from killing cells just for presenting self-proteins, self-reactive T cells are deleted from the repertoire as a result of tolerance (also known as negative selection). They include xenogenic (heterologous), autologous and idiotypic or allogenic (homologous) antigens. An autoantigen is usually a normal protein or complex of proteins (and sometimes DNA or RNA) that is recognized by the immune system of patients suffering from a specific autoimmune disease. These antigens should, under normal conditions, not be the target of the immune system, but, due to mainly genetic and environmental factors, the normal immunological tolerance for such an antigen has been lost in these patients. Tumor antigens or Neoantigens are those antigens that are presented by MHC I or MHC II molecules on the surface of tumor cells. These antigens can sometimes be presented by tumor cells and never by the normal ones. In this case, they are called tumor-specific antigens (TSAs) and, in general, result from a tumor-specific mutation. More common are antigens that are presented by tumor cells and normal cells, and they are called tumor-associated antigens (TAAs). Cytotoxic T lymphocytes that recognize these antigens may be able to destroy the tumor cells before they proliferate or metastasize. Tumor antigens can also be on the surface of the tumor in the form of, for example, a mutated receptor, in which case they will be recognized by B cells.

Examples of botanical bioactive agents include, but are not limited to PM1-004 (advanced botanical formulation for type II diabetes—Represents a multi-mechanism bioactive that: 1) in adipocytes increases adiponectin secretion, 2) in the liver lowers PEPCK expression, and 3) in muscle cells increases cellular signaling through the insulin receptor pathway, increasing glucose uptake, glycogen synthase, and glycogen accumulation.), PMI-005 (botanical bioactive, derived from a common vegetable, that inhibits gene expression of a variety of pro-inflammatory cytokines (including a-TNF, i-NOS, 1L-1b, and COX-2). Currently undergoing a human clinical trial in osteoarthritis. Also may have utility in the management of severe/life threatening inflammatory conditions, such as in the management of the septic patient.), PM1-006 (botanical bioactive, derived from a spice, that inhibits a range of inflammation-related enzymes (including a-TNF and COX-2). Also possesses range of novel bioactivities related to both lipid and glucose metabolism (RXR receptors).), PMI-007 (a powerful, centrally acting, botanical appetite suppressor which acts via a unique central pathway in the nutrient-sensing hypothalamic neurons by increasing ATP content/production. It possesses potent anorectic activity without typical CNS appetite suppressor side effects. Pre-clinical data has shown that the agent suppresses both appetite and reduces weight in animal models, while there is supporting clinical evidence of human efficacy.), PM1-008 (botanical bioactive, derived from an agricultural waste processing stream, that blocks fat accumulation/absorption and promotes weight loss via interaction with a variety of lipases including PL, LPL, and HSL.), and PMI-016 (a powerful, plant-derived anabolic/ergogenic agent, with no androgenic side effects; could be used in a range of human muscle wasting disorders, including those associated with both cancer and AIDS, as well as general aging (sarcopenia). This agent has been shown to induce protein synthesis in muscle cells (similar to IGF) and promote a reduction in protein degradation, while it has also been shown to increase growth hormone gene transcription and decrease in ubiquitin protein ligase gene transcription. PM1-016 shows no binding to testosterone receptor in contrast to anabolic steroids.).

The FDA defines drugs as products that "cure, treat, mitigate or prevent disease or that affect the structure or function of the human body." Cosmetic products are defined by the FDA as "articles intended to be rubbed, poured, sprinkled, or sprayed on, introduced into, or otherwise applied to the human body . . . for cleansing, beautifying, promoting attractiveness, or altering the appearance." Although cosmaceutical products have properties of both groups, the FDA lumps them under the definition of cosmetics, and they are not recognized as a distinct category. Because cosmaceutical products are not included in the FDA's definition of drugs, they are not subject to the same regulations, restrictions, and testing.

The composition of the present invention does not require the presence of PEO, a plasticizer or polycarbophil.

The nonaqueous, extricable composition can also include a mucosal absorbing enhancer, i.e., a substance that enhances absorption through the mucosa, mucosal coating and epithelium (otherwise known (see U.S. Patent Application Publication No. 2006/0257463) as a "penetration enhancer" or "permeability enhancer"). The mucosal absorbing enhancer may include but is not limited to polyethylene glycol (PEG), diethylene glycol monoethyl ether (Transcutol), 23-lauryl ether, aprotinin, azone, benzalkomin chloride, cetylperidium chloride, cetylmethylammonium bromide, dextran sulfate, lauric acid, lauric acid/propylene glycol, lysophosphatilcholine, menthol, methoxysalicylate, oleic acid, phosphaidylcholine, polyoxyethylene, polysorbate 80, sodium EDTA, sodium glycholated, sodium glycodeoxycholate, sodium lauryl sulfate, sodium salicylate, sodium taurocholate, sodium taurodeoxycholate, sulfoxides, and various alkyl glycosides or, as described in U.S. Patent Application Publication No. 2006/0257463, bile salts, such as sodium deoxycholate, sodium glycodeoxycholate, sodium taurocholate and sodium glycocholate, surfactants such as sodium lauryl sulfate, polysorbate 80, laureth-9, benzalkonium chloride, cetylpyridinium chloride and polyoxyethylene monoalkyl ethers such as the BRIJ® and MYRJ® series, benzoic acids, such as sodium salicylate and methoxy salicylate, fatty acids, such as lauric acid, oleic acid, undecanoic acid and methyl oleate, fatty alcohols, such as octanol and nonanol, laurocapram, the polyols, propylene glycol and glycerin, cyclodextrins, the sulfoxides, such as dimethyl sulfoxide and dodecyl methyl sulfoxide, the terpenes, such as menthol, thymol and limonene, urea, chitosan and other natural and synthetic polymers. Preferably, the mucosal absorbing enhancer is a polyol, e.g., polyethylene glycol (PEG), glycerin, maltitol, sorbitol etc. or diethylene glycol monoethyl ether (Transcutol).

In addition one can add 0.1 to 10%, preferably 0.1 to 5%, more preferably 0.1 to 3%, PEG to this mix to aid mucous layer penetration when necessary.

To improve the absorption of the bioactive ingredient by the user, it is preferred that the nonaqueous, extrudable composition has a pH that is optimized for the absorption of the given bioactive ingredient. Buffering agents may be used to control pH, including without limitation, sodium bicarbonate, potassium bicarbonate, sodium carbonate, potassium carbonate, calcium carbonate, dipotassium phosphate, potassium citrate, sodium phosphate and any other such buffer system. The buffer system may be designed to dynamically control the pH of the product taking into consideration the effect of saliva during use, i.e., a dynamic buffer system. Examples of buffer systems to obtain the preferred pH include dibasic sodium phosphate and monobasic sodium phosphate. Both are FDA accepted buffer materials used and listed in the inactive ingredients list. One example is nicotine absorption which is enhanced at PH 7 to 8. For example, for a pH of 7, the ratio of monobasic/dibasic can be 4.6/8.6; for a pH of 7.5 the ratio of monobasic/dibasic can be 1.9/11.9; and for a pH of 8.0 the ratio of monobasic/dibasic can be 0.6/13.4. These are mathematically calculated buffer numbers and will need to be adjusted according to the other ingredients added to the formula. The also need to be adjusted for the length of time designed for the dissolution of the slab dosage form on the buccal mucosa since saliva can be of a ph of about 6.8 but as it is made in larger amounts in the mouth the ph of saliva can sometimes become more basic. Thus this dynamic buffer range is adjusted in the dosage slab by the amount s of the buffer system since saliva is freshly renewable in the mouth.

The nonaqueous, extrudable composition can also, optionally, include a sweetener, such as sucralose, and/or a flavoring, e.g., peppermint, cherry, bourbon, rum, smokey rose, sweet brown & spicy, wintergreen, cool mint, bergamot, citramint, and licorice. suitable flavoring additives are commercially available from Ungerer & Company or from Tobacco Technology, Inc. of Eldersburg, Md. Most flavorings preferably use ethyl alcohol as solvent, or are solvent-free.

While a plasticizer is not required for the nonaqueous, extrudable composition, a plasticizer may also be included. The plasticizer may be present in an amount up to 30% based on the weight of the thermoplastic polymer, or present to as low a range as to be non present. The plasticizer can be, without limitation, at least one of polyethylene oxide, polypropylene glycol, polyethylene glycol, glycerin, edible polyols, glycerol, polyols, maltitol, isomalt, and reduced sugars. The use of certain plasticizers may function to increase mucoadhesion (e.g. polypropylene glycol or glycerin) and may be used for this purpose. Chitosan can be used. This material in high loading can be used in wounds to stop bleeding by causing red blood cells to form a clot. This represents a topical use of the extruded sheet material.

A coloring agent can optionally be added. The use of titanium dioxide up to 5 percent by weight results in a white or lightly colored product. Other edible pigments may be used, such as Colorcon Red #40.

In addition, up to 10%, preferably 3-5% of an acceptable silicate can be used especially if the bioactive ingredient has significant moisture content to promote flowability of composition and uniform processing.

The intention of this invention is to not only make a convenient dosage form but also to make one that added clinical benefit by virtue of better drug absorption—i.e. improved pharmacokinetics. Such improvements may take the form of faster onset, slower onset, sustained release, higher absorption of drug for a given dose as compared with other delivery vehicles, lower dosage, reduced side effects, and the like. One way in which this is accomplished is by using the oral mucosa for absorption of the drug with the surface area of the dose form against the mucosa Also the rate of dissolution of the dose form is also important to control the release of the drug. The use of a sheet dosage form for mucosal delivery increases surface area contact for the drug as compared with traditional dosage forms like sublingual tablets. Mucosal delivery allows the bioactive agent to avoid the normal first pass of the active from the GI tract (thus avoiding liver metabolism associated with release of drug in the GI tract). We allow for a slow release of the active drug by making a non aqueous, non wet cast, extruded product of from 10 to 100 mils thickness. As we will see, by modifying these thicknesses of this product and combining it with various polymers, it is possible to control the length of time of absorption (sustained release). Also, with the use of certain polymers and other excipients this product is rendered very mucoadhesive and readily sticks to the buccal cavity of the user, or sublingually, as the case may be. In addition, by the incorporation of ion exchange salts to these bioactives one can taste mask any bad drug taste. Ion exchange resin/drug combinations may additionally or alternatively be used to cause a molecular dispersion of the active or cause a nano particle dispersion of the active or help in a sustained release of the drug.

Importantly, the use of ion exchange resins in quick dissolving thin film dosage forms have been limited to taste masking and thin film as is discussed in U.S. Pat. No. 7,067,116. While the small particle size of such resinates may be particularly desirable for thin film application, their relatively low drug content for a given amount of resinate material makes it challenging to employ resinate technology in thin film due to thin film's inherent drug loading limitations discussed herein. This is the reason why in thin film use, U.S. Pat. No. 7,067,116 claims ratios of 3 to 1 and 1 to 3 of the drug/resin relationship. They have no ability to carry above the 3 multiplier figure.

There are two customary ways to taste mask bad tasting drugs that are dissolving in the mouth: coating and ion exchange. Now, in traditional cast aqueous film, either may be used, but space may prohibit optimizing each. Applicant is not aware of taste masking or sustained release being taught in extruded sheets. Like any process, extrusion process parameters (temperature and shear forces) create their own challenges. Applicant teaches herein the use of taste masking and sustained release that are consistent and complimentary to the hot melt extrusion process. However, extrusion causes some very unique problems. Therefore, in extrusion, ion exchange and cyclodextrins are two of the only methods that can tolerate the high shear. This is because in ion exchange and cyclodextrins, a major part of the active are in a sense locked in the process. In extrusion, coating size is not a limiting factor in the same way as cast film. Also, in extrusion, ion exchange and cyciodextrins are two additional technologies that can be used.

Now the additional benefits of the ion exchange are also, molecular release of active (due to molecular reaction with the exchange resin), release of nano sized active and also controlled release (depending on the strength of the bond with the exchange resin).

The present invention can be used to taste mask pharmaceuticals (including botanicals) in all major therapeutic categories should they require taste masking. Also in all major therapeutic categories, molecular or nano sized active may be desirable for more efficient uptake. In addition, the present invention provides sustained release for a given compound. Finally, the invention allows for side effect minimization by virtue principally of being able to use a lower dosage.

Ion exchange resins preferred for use in the sheets of the invention are water-insoluble and consist of a pharmacologically inert organic or inorganic matrix containing covalently bound functional groups that are ionic or capable of being ionized under the appropriate conditions of pH. The organic matrix may be synthetic (e.g., polymers or copolymers of acrylic acid, methacrylic acid, sulfonated styrene, sulfonated divinylbenzene), or partially synthetic (e.g., modified cellulose and dextrans). The inorganic matrix can also be, e.g., silica gel modified by the addition of ionic groups. The covalently bound ionic groups may be strongly acidic (e.g., sulfonic acid), weakly acidic (e.g., carboxylic acid), strongly basic (e.g., quaternary ammonium), weakly basic (e.g., primary amine), or a combination of acidic and basic groups. In general, those types of ion exchangers suitable for use in ion exchange chromatography and for such applications as deionization of water are suitable for use in these controlled release drug preparations. Such ion exchangers may be but are not limited to those described by H. F. Walton in "Principles of Ion Exchange", the entire contents of which are incorporated herein by reference, (pp. 312-343). The ion exchange resins useful in the present invention have exchange capacities below about 6 milli-equivalents per gram (meq/g) and preferably below about 5.5 meq/g.

The resin is crosslinked with a crosslinking agent selected from difunctional compounds capable of crosslinking polystyrenes; these are commonly known in the art. Preferably, the crosslinking agent is a divinyl or polyvinyl compound. Most preferably the crosslinking agent is divinylbenzene. The resin is crosslinked to an extent of about 3 to about 20%, preferably about 4 to about 16%, more preferably about 6 to about 10%, and most preferably about 8% by weight based on the total resin. The resin is crosslinked with the crosslinking agent by means well known in the art.

The size of the ion exchange resins should preferably fall within the range of about 20 to about 200 micrometers. Particle sizes substantially below the lower limit are difficult to handle in all steps of the processing. Particle sizes substantially above the upper limit, e.g., commercially available ion exchange resins having a spherical shape and diameters up to about 1000 micrometers, are gritty in liquid dosage forms and have a greater tendency to fracture when subjected to drying-hydrating cycles.

Representative resins useful in this invention include AMBERLITE IRP-69 (obtained from Rohm and Haas) and Dow XYS-40010.00 (obtained from The Dow Chemical Company). Both are sulfonated polymers composed of polystyrene cross-linked with 8% of divinylbenzene, with an ion exchange capacity of about 4.5 to 5.5 meq/g of dry resin (H+-form). Their essential difference is in physical form. AMBERLITE IRP-69 comprises irregularly-shaped particles with a size range of 47 to 149 micrometers, produced by milling the parent, large-sized spheres of AMBERLITE IRP-120. The Dow XYS-40010.00 product comprises spherical particles with a size range of 45 to 150 micrometers. Another useful exchange resin, Dow XYS-40013.00, is a polymer composed of polystyrene cross-linked with 8% of divinylbenzene and functionalized with a quaternary ammonium group; its exchange capacity is normally within the range of approximately 3 to 4 meq/g of dry resin.

The most preferred resin is AMBERLITE IRP-69. However, in less preferred embodiments, the taste masking agent need not be an ion exchange resin. In these embodiments, the taste masking agent can be, e.g., magnesium trisilicate. See, e.g., U.S. Pat. Nos. 4,650,663 and 4,581,232 to Peters et al. Taste can also be masked by polymers, such as EUDRAGIT E (Rohm and Haas), and/or cellulosics, such as ethylcellulose, and the like.

The ratio of bioactive agent to ion exchange resin or resin to bioactive agent can vary from less than 1 to 100, e.g., from 0.1:100 to 100:0.1.

Ion exchange bioactive/resin combinations however, have many other functions, principally releasing the bioactive in its molecular state and thereby enhancing absorption of the bioactive material. The slab dosage form, unlike thin film, can carry a far higher load of material and therefore for the first time in an orally dissolving sustained release dosage form makes the use of the combination possible in whatever ratio is needed as well as in higher dosage drugs. This can be inductively seen by noting the ratio limitation in U.S. Pat. No. 7,067,116. In addition the carrying ability of the slab also allows this buccal dosage form to carry penetration/absorption enhancers like (e.g. cyciodextrins or perscutol etc.) and thus aid in the use of solubility challenged bioactives.

In addition accomplishing sustained or control release through the drug ion exchange resinate complex, sustained release can be achieved by varying the dissolution of the bioactive containing matrix itself. As are seen in the examples, monolayer products with disintegration time are taught. Such times can be extended through multi layer products, including insoluble layers, as well as the addition of insoluble materials to the composition. Still, monolayer sheets are the preferred embodiment of the present invention due to their elegant processing simplicity.

Ordinary coating for taste masking and traditional encapsulation techniques for taste masking and controlled release may also be used.

The nonaqueous composition described above can be formed into a pharmaceutical product comprising a sheet or slab by extruding or hot melt shaping, as described more fully hereinafter, the sheet comprising a matrix comprising at least one thermoplastic polymer and the bioactive ingredients distributed in the matrix, the matrix being soluble on a user's oral mucosa and resulting in sustained release of the bioactive ingredients to the user.

The pharmaceutical product can be in the form of a slab that has a shape conducive, either in a folded or unfolded state, to placement on a user's mucosa, e.g., on a user's buccal mucosa, palate mucosa, sublingual mucosa, gingival mucosa, nasal mucosa, rectal mucosa, vaginal mucosa, e.g., a rectangular shape or a rounded shape. In addition the slab may be bent in half to form a V shaped architecture which will help it stay in place on the mucosa and may be preferred by some. In addition the material can be chewed once or twice and then "parked" against the mucosa.

The effectiveness of buccal delivery through sustained contact of the sheet with the buccal mucosa was demonstrated through the use a tobacco containing sheet to deliver the drug nicotine. By placing tobacco in a sheet at 25% loading—and a total tobacco amount of 75 mg and with a large surface area and taking approximately forty five minutes to dissolve in the cheek, nicotine absorption was achieved that was over five times greater than is delivered from both conventional smokeless tobacco products and a peak nicotine plasma concentration nearly 50% greater than a 2 mg nicotine policrilex chewing gum, such gum containing approximately the same amount of, or even slightly more nicotine as would commonly be understood to be contained in 75 mg of tobacco. This substantial difference in absorption is attributable to the superiority of the sheet dosage form over the medicated gum delivery of the reference product.

It is possible to avoid the need for a plasticizer when making a sheet dosage form. Sheets that rely on plasticizers for flexibility may have physical stability issues as plasticizers may, in some cases tend to volatilize over time, thus reducing flexibility of the product. Preventing a loss of plasticizer may require precautions to be taken such as expensive barrier packaging and shortened shelf life to ensure that physical stability is maintained during the product's life.

It is further desirable to avoid excess tack in sheet compositions. Since such compositions are typically rolled after manufacture and prior to final packaging, excess tackiness will require the use of s substrate to divide product layers in the roll. In addition to the cost of the substrate itself, the delamination of the sheet roll from the substrate during packaging may be problematic. Thus, a non-tacky composition and product is desirable.

The invention is not limited to oral use but may also be used topically, vaginally, rectally and internally. For example, sheets containing Chitosan can be extruded. This material in high loading can be used in wounds to stop bleeding by causing red blood cells to form a clot. The material can also contain benzocaine or lidocaine in substantial amounts due to overall loading capacity of this extruded sheet. This is yet another topical use for the extruded sheet.

The pharmaceutical product sheet preferably has a tensile strength of at least 2 lbs, preferably 4 lbs (measured according to the tension/tear test described in Example below) for efficient packaging operation.

The pharmaceutical product sheet preferably has content uniformity in the range of ±10%, more preferably ±5%. That is, the thickness of the sheet and bioactive content preferably varies over its entire surface area, as compared to an average thickness of the sheet, by at most ±10%, more preferably ±5% and most preferably 2%. The sheet can be packaged in a number of different ways, some of which will be apparent to those skilled in the art.

Those skilled in the art will understand that screw design in important to content uniformity of the sheet, to insure that proper mixing occurs and that constituent parts are not separated.

The processing temperatures are related to the type of polymer used, to the pressure used in the extruder, to the transit time through the extruder and to the viscosity of the final mix. In the examples set forth the temperatures range from 140 F to 350 F and the time of exposure is normally <3 minutes preferably <2 minutes and most preferably <90 seconds.

One packaging embodiment for the bioactive product would be in an individual pouch like container with or without child resistance as desired. As a method to prevent tacking or stickiness of each dosage unit in the pouch particles of edible powder material may be sprinkled or dusted over the sheets if required. Such dusting may be done during manufacturing of the roll stock or during the final cutting and packaging. Any edible non interference non hygroscopic powder material may be used. A bumbled surface on the sheet may also be used and serve as a non sticking agent.

This packaging can be seen in an individual sachet, similar to strip products currently marketed by Novartis Consumer Health under the Triaminic® brand, or using Cardinal Health's Defpouch® individual foil sachet. Various examples of such sachets currently exist on the market in use with various thin film drug products, including Pfizer's Benadryl®, Fleet Labs Pedialax® strips, GSK's Breathe Right Anti Snore Strip®, and Gas-X(r) strips. Thus, a single use package can include the sheet of a bioactive product comprising an extruded nonaqueous composition comprising at least one thermoplastic polymer and a bioactive agent other than tobacco, the sheet being of a size to administer a single dose of the bioactive agent to a user, and a package in which the sheet is sealed.

Another, separate method of reducing tacking or stickiness of sheets is to manufacture a sheet without a smooth surface area. The smoother the surface area, the greater the contact surface area between sheet and container. Conversely, a rougher surface area will tend to reduce the contact surface area between same. As a general matter, such reduction in contact surface area will reduce the tendency to tack or stick. Rougher surface area can be achieved in various ways. For example insoluble particles can be used of sufficient size to leave a grainy texture in the final product. Such insoluble particles may be inactive or active ingredients including ingredient particles. The surface of the sheet may also be physically disrupted using textured rollers—essentially embossing roughness into the surface of the sheet.

Ink jet printing with edible inks may be used to print labels, brand names or other images on the product.

The product can be manufactured by hot melt shaping or, in particular, by hot melt extruding the nonaqueous composition described above. Now the most efficient way known to applicant to make this product is to use hot melt extrusion technology so that the product is economically feasible and has fine rheoiogical properties. The product may be extruded in state of the art single or multiple screw extruders, preferably with appropriate cooling jackets, tubes and pumps and vents. It may be desirable with certain compositions to draw a vacuum over the vents. For example drawing vacuum over the extruder vents may be useful when using mixtures that may have excess moisture in them. In that case, operating temperature should be adjusted to compensate for boiling point lowering and elevation caused by various flavor packages.

Alternatively, the product can be melted between, e.g., foil, layers on a lower hot plate, and pressed to shape and desired thickness with an upper hot surface. The foil can be cooled with a cooling liquid to cool the product, and the product peeled from the foil layers. Other hot melt systems like heated guns may also be used to melt the composition.

However, a preferred method for making the pharmaceutical product is to extrude the nonaqueous composition described above through an extruder to form an extruded slab or sheet of the nonaqueous composition. Preferably, extruding of the composition is carried out without injecting gas into the composition.

The extruded sheet is then cut to form a plurality of small slabs, the smaller slabs having the appropriate size and shape, e.g., the sizes and shapes consequent with a comfortable feel in the mouth and against the buccal, lingual, sublingual or gingival mucosa. Such cutting into pieces may be done using a plethora of existing cutting methods, including F&G rotary blade stack and pack machines, guillotine style cutters, die cut machines, Doyen Medipharm individual sachet producing equipment, etc.

In many cases, any portions of the extruded sheet discarded after cutting may be recycled to an inlet of the extruder. For example, the product may be subject to certain product loss in packaging such as, for example, the edges of the roll stock may be trimmed or cut off to ensure that all products have uniform appearance. Additionally, waste might be created in the packaging step. To re-use such loss product, the loss product may be chipped and added to the composition placed in the extruder.

This method for re-use allows for the use of the non-rectangular shapes. Such shapes can be die cut from the sheet but are typically disfavored in the wet cast thin film industry because of the resulting product loss (theoretically equal to the area of the rectangle minus the area of the die cut dose and in practice larger).

It is important to point out that in this system the normal wasted chips can be reused since they have the same composition as the mix they are placed in for re-extrusion and hence do not disturb the content uniformity of the finished product. This is not anticipated to be required however as the throughput % in nonaqueous extrusion is very high since there is practically no loss in the mixing step, and there is very little loss associated with the commencement of extrusion of acceptable product.

Instead of immediately cutting the extruded sheet, extruded sheet may be wound about a roll to form a roll of the extruded sheet. The extruded product is non-tacky and can be rolled without a backing and without the layers of the roll sticking to one another. The roll can be slit using a conventional slitter perpendicularly to an axis of the roll in a number of places to form a plurality of rolls or bobbins having a width of, e.g., 1 inch. These slit bobbins can then be cut into pieces. Slitting can also occur by passing the extruded sheet over a slit blade network such that it is would on the bobbin already slit—thus slitting the product after extrusion and prior to roll up.

Identifiers, including without limit, brand names and designs may be printed on each piece using conventional edible ink jet technology as is currently used in the thin film drug delivery industry.

For thicker sheets it may be desirable to add chewing gum chickle to the exterior of the sheet. This provides an initial pleasant taste and makes placement in the mouth easier.

Thicker sheets, e.g., sheets greater than 10 mils, preferably greater than 25 mils, may be chewed by the user even without the addition of chickle. They also may be chewed and then parked in the lip or cheek fold.

Immediately after extrusion, the sheet may be passed around a portion of at least one roller. The at least one roller may be smooth or may be textured to provide a textured surface one side or both sides of the extruded sheet. The textured surface on one or both sides can aid or retard mucoadhesion. For example, the at least one roller may be graveured to provide a design on a surface on at least one side of the extruded sheet.

In yet another alternative, the sheet may be passed, after extrusion, through dual heated rollers to assure an absolute uniform thickness corresponding to the distance between the rollers. Better heat transfer is obtained if both rollers are heated but it is not absolutely necessary. If the heat makes the sheet tacky, a backing substrate which is siliconized or made non-stick can be provided, which can go through on one or both sides of the sheet so as to prevent sticking to the roller(s) and then get wound up right away on a take-up spool, or the rollers can be made to have a non-stick (e.g., Teflon) surface. The backing substrate just keeps sticky polymers from sticking to the rollers. Also to improve speed of process one may include chilling rolls which will lower the temperature of the sheet post heating/flattening stage. Certain thermoplastic polymers require more plasticizer so that, for example, pullulan may require 20-30% of a glycerin to plasticize and yet not be sticky while other polymers like HPC LF cannot take as much as 3 or 4% glycerin without being tacky. It is a matter of the Tg of the native polymer. HPC LF has a much lower Tg than pullulan and, therefore, does not need as much interruption of the intermolecular bonding, which plasticizers tend to do. The LF polymer is sticky because the Tg of the plasticized polymer is lower than room temperature. If the Tg was, e.g., 45° C. then it would not be tacky to the touch at room temperature. However, if the temperature is raised to 45° C., the same polymer would be tacky. That is why to have low extrusion temperature polymers one should look for low Tg polymers (like HPC) or polymers that are crystalline and melt at low temperature (like PEO).

In some cases, it may be desirable for the sheet to be thicker on one end (across its width) then the other, i.e., basically a wedge shaped sheet. In extrusion, this is easily accomplished by the die being wider on one side than the other.

The extruder may be a single screw extruder. In one embodiment of the invention, the nonaqueous composition is extruded through the single screw extruder. Alternatively, the extruder may be a double screw extruder with a pump to pump the nonaqueous composition through a die thereof at constant pressure. The extruder may comprise a gear pump and coat hanger-type die to control the pressure in the extruder and the thickness of the sheet across a width of the sheet. It also may include a very accurate feeder such that the operating pressure is kept in tight parameters. Also in either embodiment, beta type gauges can constantly monitor product thickness and even be part of a feedback network to the pressure control points. Thus, the thickness of the extruded sheet can be controlled by monitoring the thickness of the extruded sheet using a thickness (e.g., beta). gauge system, and controlling a feeder feeding the extruder and a pressure of a pump to pump the nonaqueous composition through a die on the basis of the monitored thickness.

The extruder dye can be provided with a small tit or tits that cause a mark or line by indentation. The mark or line can serve to indicate a fold mark on the sheet for user for reasons mentioned above as V architecture. Preferably, the sheet has a tensile strength of at least 2 lbs, preferably 4 below) for efficient packaging operation. Efficiency in packaging means packaging speed/output and yields. A good tensile strength means that the sheet stock will not break under the tensions placed on such stock during the packaging process. Breakage from such tensions reduces output through down time and also reduces yield as the packaging machine must be rethreaded.

Preferably, the composition is exposed to heat in processing for less than 90 seconds to reduce heat exposure to the bioactive ingredient.

During extrusion, it is possible to provide supercritical liquid injection, e.g., $CO_2$ liquid, to the extruder to make a quick dissolve extruded foam slab.

The present invention may be used to make multilayer products consisting of multiple, extruded sheets. Such multilayer composites are laminates may contain one or more layers with or without bioactive ingredients. Additional layers may be used to employ varying dissolution rates, including insoluble layers. Another embodiment includes the use of additional layers with pH buffer systems to dynamically control pH to optimize absorption of the bioactive. Layers may also be used to increase the bioactive content of the total composition. Additional layers may be extruded directly on top of or in conjunction with (coextrusion) previously extruded layers in the manufacturing process.

Enzymatically mediated materials may be used in the composition such as CMC enzyme to aid in the breakdown of the slab or sheet in the wet environment of the mouth. Another example is the addition of amylase to the composition (which is also naturally occurring in saliva) to aid in the dissolution of starch content.

It may be desirable in certain embodiments of the product to enhance the perception of tingling by using certain topically effective agents. For example menthol may provide a topical sensation akin to that associated with efficacy of the bioactive ingredient. There are other agents that can cause this, e.g., peppermint, spearmint, wintergreen and many other agents too numerous to mention but known to one skilled in this art.

Additionally, it may also be desirable, to aid absorption, to create effervescence in the sheet.

Flowability of the dry blend into the extruder is important. Blends which have agglomerations or tend to agglomerate may result in uneven, non-uniform extruded compositions. In certain instances therefore it is desirable to use a flow agent, like a silica derivative (e.g. calcium silicate), to promote flowability and resulting evenness and uniformity of the finished product.

Flowability may also be engendered through proper mixing techniques. For example, the use of a high shear mixer may be necessary to prevent the formation of "fish eyes" or agglomerations from flavor or residual moisture in ingredients. High shear mixing is essential when any product with moisture (usually residual to prior ingredient process) is added to the product mix. Once fish eyes or agglomerations are formed they are extremely difficult to eliminate; hence high shear mixing must be employed from the beginning. An example is the use of botanical bioactive ingredient that has high residual moisture, when added without high shear agglomerations are formed which result in poor uneven sheets. If that same material is added with a high shear mixture such as a high speed Cuisinart blade type mixture, this does not occur and the sheet is excellent.

Figure 2:
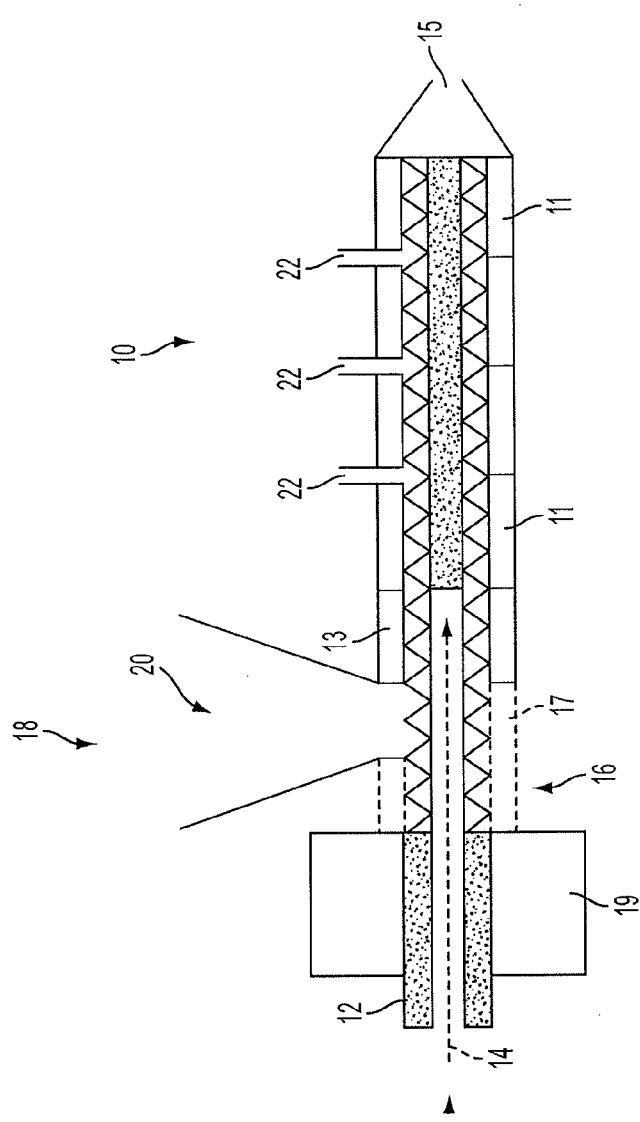
FIG. 2 is a schematic diagram showing one example of an extrusion process that can be used in the manufacturing method for the pharmaceutical product of the present invention.

According to one aspect of the present invention, the bioactive product can be manufactured by the method of the nom-limitative example shown schematically in FIGS. 1 and 2.

As shown in FIG. 1, all solid materials are weighed with scale 2. and premixed in mixer & chopped recycle. The flavors and plasticizers are also weighed and can be mixed in blend mixer 4. The blend in blend mixer 4 can be added to a mixer with choppers 6, to which chopped recycle can also be added, where mixing is finished. The mix can then be stored in finish mix container 8.

As distinguished from aqueous compositions, the non-aqueous compositions of the present invention are easier to mix. Non-aqueous compositions imply lower mixing volumes and the absence of degassing issues. Conventional mixers may be used. Feeding of the mix into the extruder must be performed at a controlled rate (e.g., using a ktronic feeder) to ensure constant pressure in the extruder and at the slot die.

FIG. 2 is a schematic diagram showing one example of an extrusion process/extruder 10 that can be used in the manufacturing method for the bioactive product of the present invention. A typical single screw extruder with heating zones 11, cooling zones 13, die 15 and drive 19 is modified according to this embodiment to better process the composition of the present invention. Cooling of the front section of extruder screw shaft 12 can be accomplished by a water-cooling bore 14. Cooling of the barrel 16 and the area around the feeding section 18, fed by feeding hopper 20, by additional barrel and feeding section cooling zones 17, keeps the product from melting and plugging the hopper 20. The screw design is well balanced to keep the screw 12 full with no cavitation to keep pressure constant. Venting ports 22 are provided to remove vapors/gases to keep the sheet free of bubbles and smooth.

Figure 3:
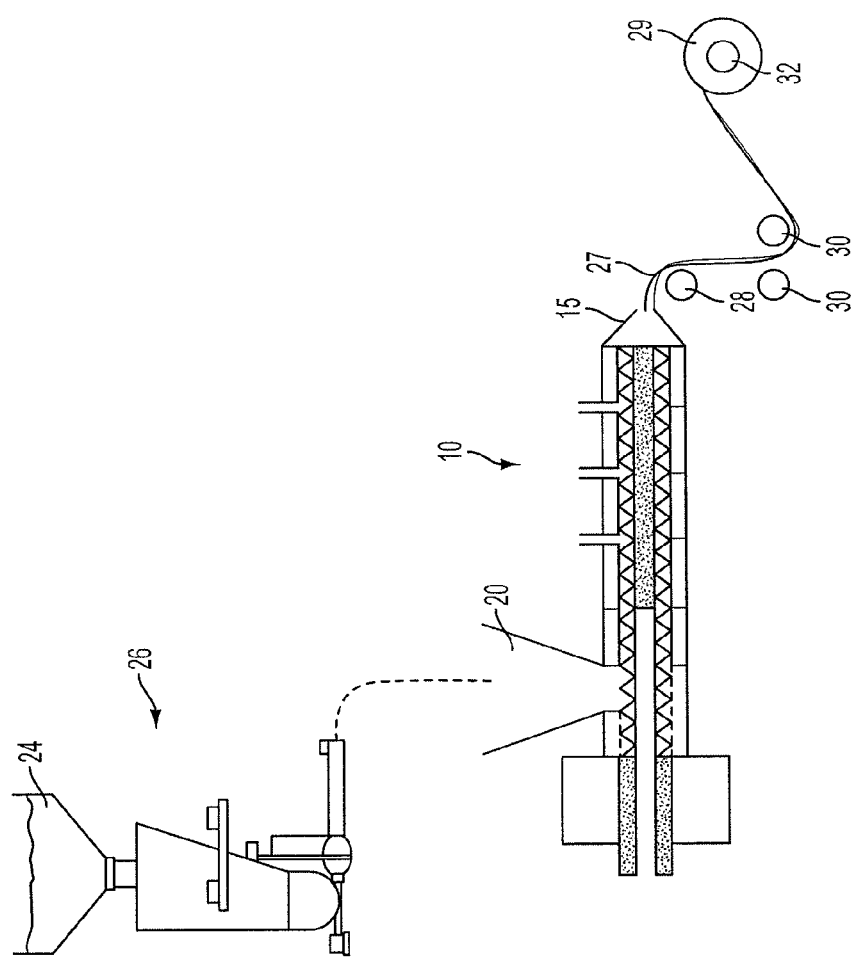
FIG. 3 is a schematic diagram showing one example of a small scale extrusion process that can be used in the manufacturing method for the pharmaceutical product of the present invention.

FIG. 3 is a schematic diagram showing one example of a small scale extrusion process that can be used in the manufacturing method for the bioactive product of the present invention. In FIG. 3, the complete mix 24, including solids and liquids, is fed from a loss in weight feeder 26 to the hopper 20 of the extruder 10. The extruded sheet 27 coming from die 15 is passed around a chill roll 28 and over portions of rollers 30. It is then wound by a torque winder 32 onto a roll 29.

Figure 4:
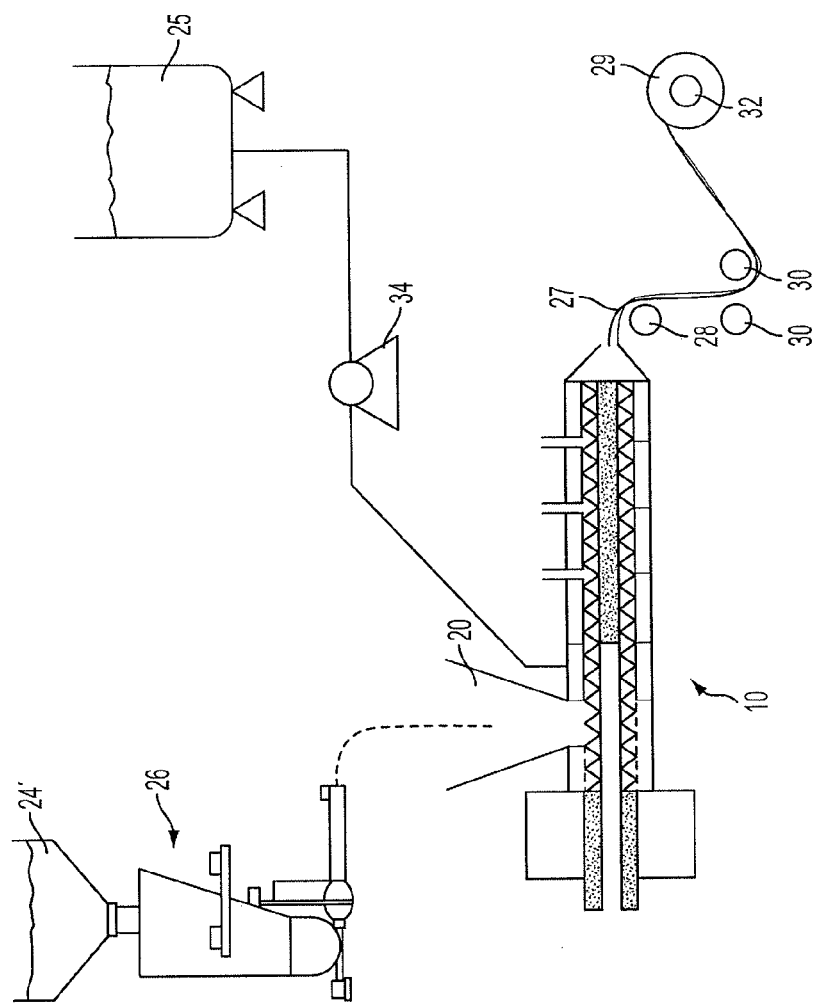
FIG. 4 is a schematic diagram showing one example of a medium scale extrusion process that can be used in the manufacturing method for the pharmaceutical product of the present invention.

FIG. 4 is a schematic diagram showing one example of a medium scale extrusion process that can be used in the manufacturing method for the pharmaceutical product of the present invention. FIG. 4 shows a process similar to that of FIG. 3 but allows for separate feeding of a solids blend 24' and a flavors/plasticizers blend 25 in liquid form by proportioning pump 34. This embodiment has the advantages that it reduces cross contamination and reduces clean up time.

Figure 5:
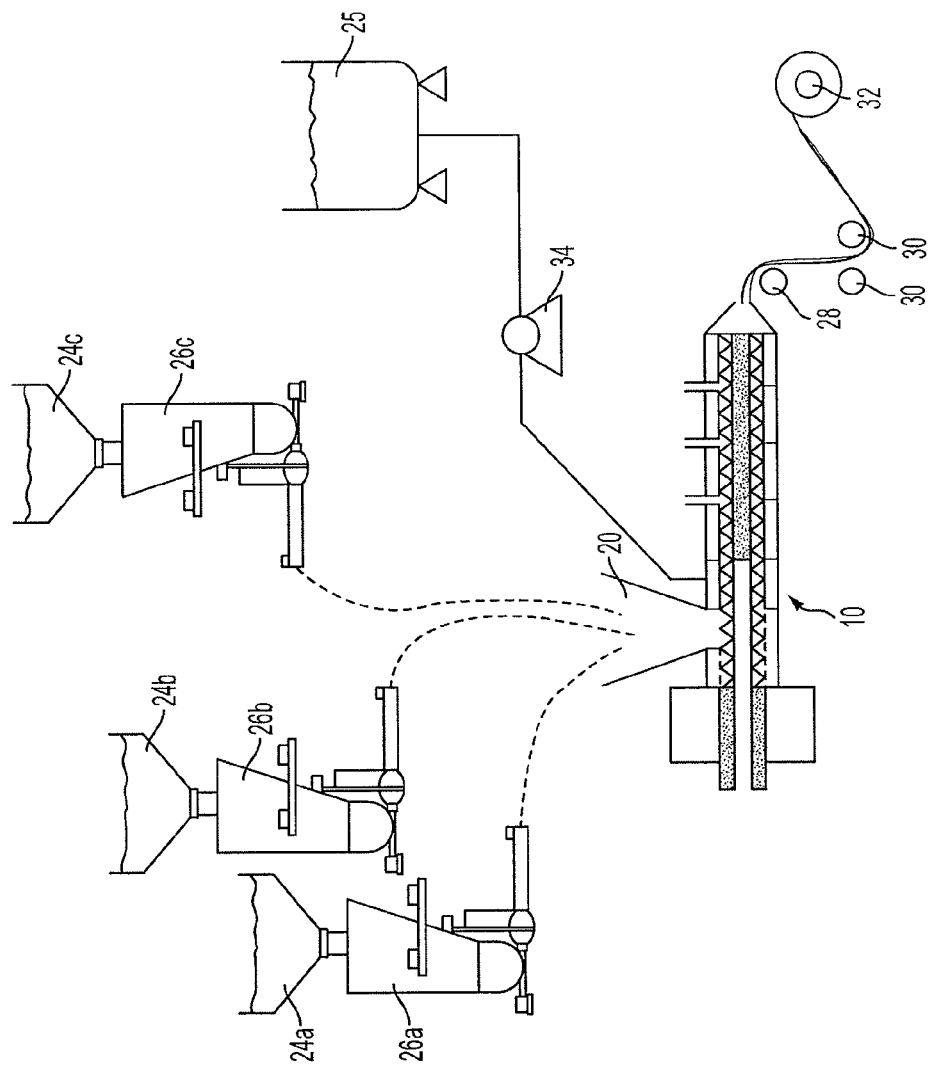
FIG. 5 is a schematic diagram showing one example of a large scale extrusion process that can be used in the manufacturing method for the pharmaceutical product of the present invention.

FIG. 5 is a schematic diagram showing one example of a large scale extrusion process that can be used in the manufacturing method for the pharmaceutical product of the present invention. FIG. 5 shows a process similar to that of FIG. 4 but allows for separate feeding of polymer 24a, small percentage solids blend 24b and pharmaceutical bioactive 24c using loss in weight feeders 26a, 26b and 26c, respectively. This embodiment has the advantages that it reduces cross contamination, reduces clean up time, reduces the number of batches and reduces mixer size.

Figure 6:
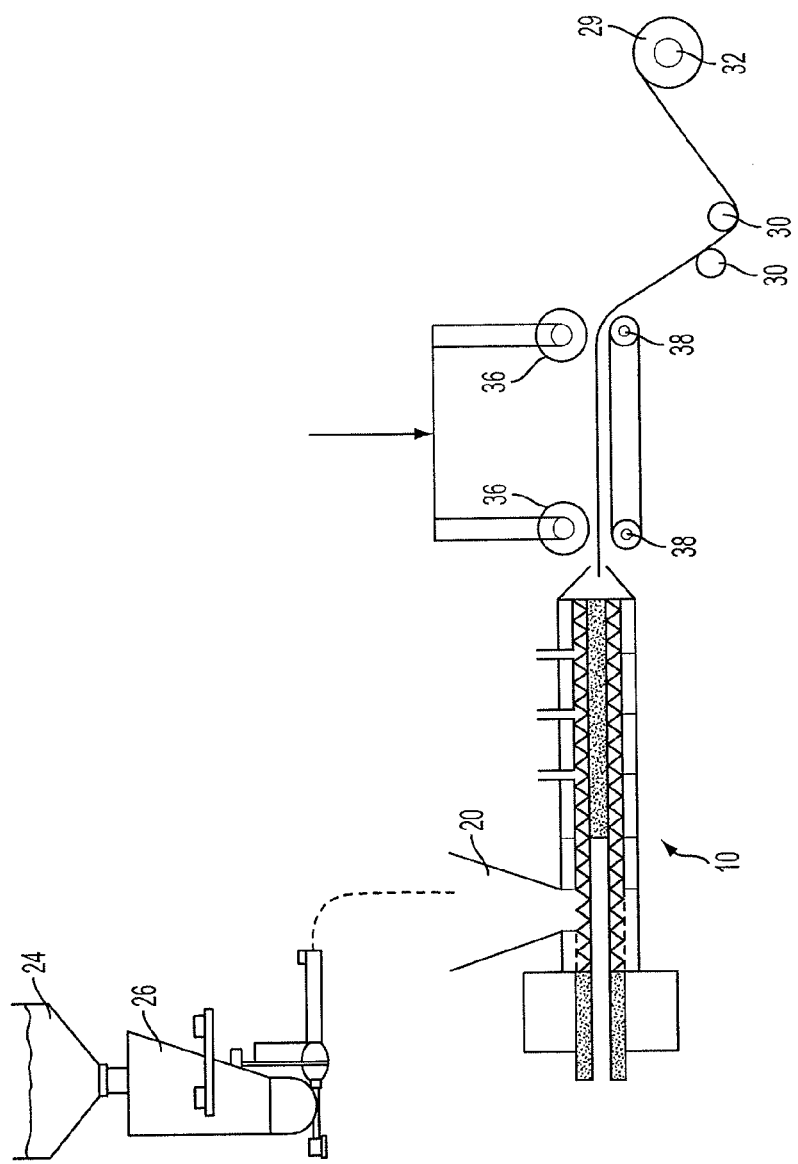
FIG. 6 is a schematic diagram showing one example of an extrusion process with optional compression rollers that can be used in the manufacturing method for the pharmaceutical product of the present invention.

FIG. 6 is a schematic diagram showing one example of an extrusion process with optional compression rollers 36 and heated rollers 38 that can be used in the manufacturing method for the pharmaceutical product of the present invention assure uniform thickness across the web substrate.

Another aspect of the invention is a method for delivering the bioactive agent of the product to a user by providing a sheet comprising an extruded nonaqueous composition comprising at least one thermoplastic polymer and one or more bioactive agents, and placing the sheet in the buccal cavity of, on the palate of or sublingually or anally or vaginally in the user or topically on the user. The present invention enables the bioactive agent to be delivered to the user in a bioavailable form. The sheet can be folded at approximately a mid-point of its length to form a V-shaped folded sheet before placing the sheet in, e.g., the buccal cavity.

In using the bioactive sheet of the present invention, adhering the sheet to the buccal cavity and increasing the disintegration or dissolution time can be achieved by the user folding the sheet to form what is referred to herein as the "V architecture". The bioactive sheet can be sold or cut to dimension required for comfort and usage. This cut pharmaceutical sheet can then be folded by the consumer or manufacturer at approximately the midpoint of the sheet, making for a sheet of 0.5 x by y. The term "V Architecture" refers to the resulting shape. The pharmaceutical sheet is now thicker and displays spring-like characteristic to push outwards. The sheet is then placed in the buccal cavity and the spring like characteristic makes the pharmaceutical sheet adhere more easily in the buccal cavity no matter how placed.

The residence time of the bioactive agent in the extruder can be reduced by using appropriately precise feed device of the dry blend, together with a proper screw design so that the use of a pump can sometimes be avoided.

Additionally, the bioactive agent can be injected into the extruder after the hold melt base has already been formed. It has also been seen that for larger diameter screws above an inch or so, it is desirable to have a cooling line run in and out of the screw core.

The following are nonlimitative examples of the present invention. The process equipment used for Examples B, C, and D was:

Scale: Ohaus Model CD-11
Mixer: Cuisinart 14 cup processor
Feeder: Randcastle Volumetric Conveyer Type
Extruder: Randcastle Taskmaster 1000 triple vented 36/1 LD with triple elongated patented screw
Slab exit: Randcastle 6 inch flexible lip die with 2 inch chill roll and torque winder Example A The following ingredients were mixed in a dry blend, using multiple batches in a Hamilton 8 cup Hamilton Beach/Cuisinart style food processor for a total quantity of 10 kg's.

| Ingredient | % | Supplier |
| --- | --- | --- |
| HPC LF | 58.75 | Aqualon (Hercules) |
| Propylene Glycol FCC, NF | 3 | Spectrum |
| Xylitol NF | 5.25 | Roquette |
| Bitter Masker | 2 | Ungerer |
| Sucralose | 2 | Tate & Lyle |
| Snuff | 25 | Bruton |
| Peppermint Flavor | 2 | Ungerer |
| TiO2 | 2 | DNP International |
| Total | 100 | |

The dry blend was fed into a single screw extruder (L/D ration 36) with rpm set at 180 and a barrel temperature set at 230 F for the initial zone and 300 F for subsequent zones and the slot die. The extruder was fed at a rate of 7 kg of material per hour. The liquid base of the flavor was vented from the extruder. The slot die was set at 30 mils. The slot die had a width of ten inches. The sheet was extruded with the take off rollers and showed a thickness of 13 mils and was rolled onto a roller without the use of any backing materials. Residence time of the material in the extruder was approximately ninety seconds. Thickness was measured and determined to be uniform across the web and through the roll.

The sheet was flexible and robust. Pieces were cut into dimensions of 1 in. by 1 in. The pieces could be bent 180 degrees without breaking. These pieces were folded and placed in the upper gum and showed a dissolution time of 12-25 minutes. When placed in the lower gum, where greater saliva is present, they folded samples showed a dissolution time of 8-15 minutes. The long period of dissolution resulted in a distinct minty breath for a long period. This far exceeded the lasting effect of traditional cast thin film and cast film breath fresheners. It was observed that the composition of this example, but without tobacco, would be highly useful as a long lasting breath freshener.

Example B

The following ingredients were mixed in a dry blend, using multiple batches in a Hamilton 8 cup Hamilton Beach/Cuisinart style food processor for a total quantity of 3 kgs.

| Ingredient | % | Supplier |
| --- | --- | --- |
| HPC ELF | 56 | Aqualon (Hercules) |
| Xylitol NF | 5.5 | Roquette Maltisorb P200 |
| Bitter Masker | 3 | Ungerer |
| Sucralose | 2.5 | Tate & Lyle |
| Dextromethorphan-ion exchange resinate (46.9% Dextromethorphan/53.1% Polacrilex Resin) | 11.25 | Cambrex |
| Ca Silicate | 6 | J M Huber |
| Ca Co3 | 11 | Specialty Minerals |
| Cherry Flavor | 2 | Ungerer |
| Red | .75 | Keystone Red # 40 |
| TiO2 | 2 | DNP International |
| Total | 100 | |

The dry blend was fed into a single screw extruder (L/D ration 36) with rpm set at 180 and a barrel temperature set at 160 F for the initial zone and subsequent zones and the slot die increasing to 240 F. The extruder was fed at a rate of 7 kg of material per hour. The liquid base of the flavor was vented from the extruder. The slot die was set at 30 mils. The slot die had a width of ten inches. The sheet was extruded with the take off rollers and showed a thickness of 15 mils and was rolled onto a roller without the use of any backing materials. Residence time of the material in the extruder was approximately ninety seconds. Thickness was measured and determined to be uniform across the web and through the roll.

The sheet was flexible and robust. Pieces were cut and could repeatedly be bent 180 degrees without breaking. These pieces were sampled by 4 healthy volunteers and each volunteer reported that the taste was excellent—thereby confirming that the integrity of the resinate bond was maintained through the extrusion process.

The drug/resinate particles were observed in the final sheet, with their appearance unchanged by the process. These pieces were placed unseparated into a container and were observed to maintain separation of one piece from another (i.e. not sticking); nor was tack observed in the roll stock.

Example C

The following ingredients were mixed in a dry blend, using multiple batches in a Hamilton 8 cup Hamilton Beach/Cuisinart style food processor for a total quantity of 4 kgs.

| Ingredient | % | Supplier |
|---|---|---|
| HPC ELF | 54 | Aqualon (Hercules) |
| Xylitol NF | 5 | Roquette Maltisorb P200 |
| Bitter Masker | 1.5 | Ungerer |
| Sucralose | 2 | Tate & Lyle |
| Phenylephrine-ion exchange resinate (41.4% Phenylephrine/51.6% Sodium Polystyrene Sulfonate resin) | 16 | Cambrex |
| Ca Silicate | 4 | J M Huber |
| Ca Co3 | 11 | Specialty Minerals |
| Peppermint | 1.5 | Ungerer |
| TiO2 | 2 | DNP International |
| Total | 100 | |

The dry blend was fed into a single screw extruder (L/D ration 36) with rpm set at 180 and a barrel temperature set at 160 F for the initial zone and subsequent zones and the slot die increasing to a maximum of 240 F. The extruder was fed at a rate of 7 kg of material per hour. The liquid base of the flavor was vented from the extruder. The slot die was set at 30 mils. The slot die had a width of ten inches. The sheet was extruded with the take off rollers and showed a thickness of 16 mils and was rolled onto a roller without the use of any backing materials. Residence time of the material in the extruder was approximately ninety seconds. Thickness was measured and determined to be uniform across the web and through the roll.

The sheet was flexible and robust. Pieces were cut and could repeatedly be bent 180 degrees without breaking.

These pieces were sampled by 4 healthy volunteers and each volunteer reported that the taste was excellent—thereby confirming that the integrity of the resinate bond was maintained through the extrusion process. The drug/resinate particles were observed in the final sheet, with their appearance unchanged by the process. Dissolution time was approximately 20+ minutes with good buccal adhesion. These pieces were placed unseparated into a container and were observed to maintain separation of one piece from another (i.e. not sticking), nor was tack observed in the roll stock.

Example D

The following ingredients were mixed in a dry blend, using multiple batches in a Hamilton 8 cup Hamilton Beach/Cuisinart style food processor for a total quantity of 4 kgs.

| Ingredient | % | Supplier |
|---|---|---|
| HPC ELF | 54 | Aqualon (Hercules) |
| Xylitol NF | 5 | Roquette Maltisorb P200 |
| Bitter Masker | 2 | Ungerer |
| Sucralose | 2 | Tate & Lyle |
| Dextromethorphan-ion exchange resinate (46.9% Dextromethorphan/53.1% Polacrilex Resin) | 23 | Cambrex |
| Ca Silicate | 4 | J M Huber |
| Ca Co3 | 5.25 | Specialty Minerals |
| Cherry Flavor | 2 | Tobacco Technology |
| Red | .75 | Keystone Red # 40 |
| TiO2 | 2 | DNP International |
| Total | 100 | |

The dry blend was fed into a single screw extruder (L/D ration 36) with rpm set at 180 and a barrel temperature set at 160 F for the initial zone and subsequent zones and the slot die increasing to a maximum of 240 F. The extruder was fed at a rate of 7 kg of material per hour. The liquid base of the flavor was vented from the extruder. The slot die was set at 30 mils. The slot die had a width of ten inches. The sheet was extruded with the take off rollers and showed a thickness of 16 mils and was rolled onto a roller without the use of any backing materials. Residence time of the material in the extruder was approximately ninety seconds. Thickness was measured and determined to be uniform across the web and through the roll.

The sheet was flexible and robust. Pieces were cut and could repeatedly be bent 180 degrees without breaking.

These pieces were sampled by 4 healthy volunteers and each volunteer reported that the taste was excellent—thereby confirming that the integrity of the resinate bond was maintained through the extrusion process. The drug/resinate particles were observed in the final sheet, with their appearance unchanged by the process. Dissolution time was approximately 20+ minutes with good buccal adhesion. These pieces were placed unseparated into a container and were observed to maintain separation of one piece from another (i.e. not sticking), nor was tack observed in the roll stock.

Example E

The following ingredients were mixed in a dry blend, using multiple batches in a Hamilton 8 cup Hamilton Beach/Cuisinart style food processor for a total quantity of 8 kgs.

| Ingredient | % | Supplier |
|---|---|---|
| HPC ELF | 54 | Aqualon (Hercules) |
| Xylitol NF | 5 | Roquette Maltisorb P200 |

| Ingredient | % | Supplier |
|---|---|---|
| Bitter Masker | 1.5 | Ungerer |
| Sucralose | 2 | Tate & Lyle |
| Chitosan | 25 | |
| Ca Silicate | 2 | J M Huber |
| Ca Co3 | 7 | Specialty Minerals |
| Peppermint | 2 | Ungerer |
| TiO2 | 2 | DNP International |
| Total | 100 | |

The product was extruded in accordance with the process described in Example B. This resulted in a very nice roll of chitosan sheet that was cut to various sized pieces. The product has uses for systemic use and for wound care (obviously for which the flavor would be omitted). Product was 16 mils thick.

Example F

The following ingredients were mixed in a dry blend, using multiple batches in a Hamilton 8 cup Hamilton Beach/Cuisinart style food processor for a total quantity of 5 kgs.

| Ingredient | % | Supplier |
|---|---|---|
| HPC ELF | 52 | Aqualon (Hercules) |
| Xylitol NF | 5.25 | Roquette Maltisorb P200 |
| Sucralose | 2 | Tate & Lyle |
| Benzocaine USP | 5 | Changzhou Sunlight |
| Corn starch | 31 | Argo |
| Red # 40 | .75 | Colorcon |
| Cherry | 2 | Ungerer |
| TiO2 | 2 | DNP International |
| Total | 100 | |

The product was extruded in accordance with the process of the example B and the web was found to be uniform at 15 mils thickness. Two hundred twenty mg pieces were cut from the web using a die cut punch. Four healthy volunteers tested the product both on the tongue to release active on the throat and in the buccal cavity. Numbing effect was perceived very strongly and the product lasted for twenty to thirty minutes in the buccal cavity.

The product demonstrated a fairly high level of tackiness, and this was attributed to the tendency of benzocaine to act as a plasticizer. It was observed that a backing layer or dusting should be used to keep the product layers from adhering to one another in the roll stock.

Example G

The following ingredients were mixed in a dry blend, using multiple batches in a Hamilton 8 cup Hamilton Beach/Cuisinart style food processor for a total quantity of 5 kgs.

| Ingredient | % | Supplier |
|---|---|---|
| PEO 1105 | 5.5 | Dow (Colorcon) |
| PEO N80 | 30.94 | Dow (Colorcon) |
| PEO N10 | 13.75 | Dow (Colorcon) |
| HPC LF | 4.81 | Aqualon |
| Maltitol | 12.75 | Roquette |
| Sucralose | 2 | Tate & Lyle |
| Tobacco | 25 | Bruton |
| Vitamin E TPGS | 2 | Eastman Chemical |
| Peppermint Flavor | 2 | Ungerer |
| Citric Acid NF CL-131 | 1 | Spectrum |
| TiO2 | 0.25 | DNP International |
| Total | 100 | |

The dry blend was fed into a single screw extruder (L/D ration 36) with rpm set at 180 and a barrel temperature set at 230 F for the initial zone and 300 F for subsequent zones and the slot die. The extruder was fed at a rate of 7 kg of material per hour. The liquid base of the flavor was vented from the extruder. The slot die was set at 30 mils. The slot die had a width of ten inches. The sheet was extruded with the take off rollers and showed a thickness of 12 mils and was rolled onto a roller without the use of any backing materials. Residence time of the material in the extruder was approximately ninety seconds.

Thickness was measured and determined to be uniform across the web and through the roll.

The sheet was flexible and robust. Pieces were cut into dimensions of 1 in. by 1 in. The pieces could be bent 180 degrees without breaking. This formula demonstrated mucoadhesion.

Example H

The following ingredients were mixed in a dry blend, using multiple batches in a Hamilton 8 cup Hamilton Beach/Cuisinart style food processor for a total quantity of 10 kgs.

| Ingredient | % | Supplier |
|---|---|---|
| HPC LF | 53.75 | Aqualon (Hercules) |
| Propylene Glycol FCC, NF | 3 | Spectrum |
| Xylitol NF | 5.25 | Roquette |
| Bitter Masker | 2 | Ungerer |
| Sucralose | 2 | Tate & Lyle |
| Tobacco | 30 | Bruton |
| Peppermint Flavor | 2 | Ungerer |
| TiO2 | 2 | DNP International |
| Total | 100 | |

The dry blend was fed into a single screw extruder (L/D ration 36) with rpm set at 180 and a barrel temperature set at 230 F for the initial zone and 300 F for subsequent zones and the slot die. The extruder was fed at a rate of 7 kg of material per hour. The liquid base of the flavor was vented from the extruder. The slot die was set at 30 mils. The slot die had a width of ten inches. The sheet was extruded with the take off rollers and showed a thickness of 13 mils and was rolled onto a roller without the use of any backing materials. Residence time of the material in the extruder was approximately ninety seconds. Thickness was measured and determined to be uniform across the web and through the roll.

The sheet was flexible and robust. Pieces were cut into dimensions of 1 in. by 1 in. The pieces could be bent 180 degrees without breaking. These pieces were folded and placed in the upper gum and showed a dissolution time of 12-25 minutes. When placed in the lower gum, where greater saliva is present, they folded samples showed a dissolution time of 8-15 minutes.

Example I

The following ingredients were mixed in a dry blend, using multiple batches in a Hamilton 8 cup Hamilton Beach/Cuisinart style food processor for a total quantity of 11 lbs.

| Ingredient | % | Supplier |
|---|---|---|
| HPC LF | 59.25 | Aqualon (Hercules) |
| Propylene Glycol FCC, NF | 2 | Spectrum |
| Xylitol NF | 5.25 | Roquette |
| Bitter Masker | 2 | Ungerer |
| Sucralose | 2 | Tate & Lyle |
| Tobacco | 25 | Bruton |
| Peppermint | 2 | Ungerer |
| TiO2 | 2 | DNP |
| Glycerin | .5 | Lognis |
| Total | 100 | |

This composition was extruded in accordance with the process set forth in example A, and resulted in a similarly uniform product web. As expected, the reduction in glycerin reduced the tackiness of the resulting sheet.

Example J

The following ingredients were mixed in a dry blend, using multiple batches in a Hamilton 8 cup Hamilton Beach/Cuisinart style food processor for a total quantity of 6 lbs.

| Ingredient | % | Supplier |
|---|---|---|
| HPC ELF | 61 | Aqualon (Hercules) |
| Xylitol NF | 6 | Roquette |
| Bitter Masker | 2 | Ungerer |
| Sucralose | 2 | Tate & Lyle |
| Tobacco | 25 | Bruton |
| Peppermint Flavor | 2 | Ungerer |
| TiO2 | 2 | DNP International |
| Total | 100 | |

This composition was extruded in accordance with the process set forth in example A, and resulted in a similarly uniform product web. The removal of the plasticizer contained in other formulas, i.e. Propylene Glycol, did not adversely affect the flexibility and strength of the sheet. Samples were cut from the roll, and maintained their flexibility and strength over an observed period of sixty days. The absence of a plasticizer is desirable for stability (and lack of tackiness) in extreme climatic conditions.

Example K

The following ingredients were mixed in a dry blend, using multiple batches in a Hamilton 8 cup Hamilton Beach/Cuisinart style food processor for a total quantity of 6 lbs.

| Ingredient | % | Supplier |
|---|---|---|
| HPC LF | 57 | Aqualon (Hercules) |
| Xylitol NF | 5 | Roquette |
| Sucralose | 2 | Tate & Lyle |
| Starch | 6.25 | Argo |
| Tobacco | 25 | Bruton |
| Cherry | 2 | Ungerer |
| TiO2 | 2 | DNP |
| Red #40 | .75 | Lognis |
| Total | 100 | |

The dry blend was fed into a single screw extruder (L/D ration 36) with rpm set at 180 and a barrel temperature set at 260 F for the initial zone and 260 F for subsequent zones and the slot die. The extruder was fed at a rate of 7 kg of material per hour. Some of the liquid base volatiles of the flavor were vented from the extruder. The slot die was set at 30 mils. The slot die had a width of ten inches The sheet was extruded with the take off rollers and showed a thickness of 13 mils and was rolled onto a roller without the use of any backing materials. Residence time of the material in the extruder was approximately ninety seconds. Thickness was measured and determined to be uniform across the web and through the roll.

The sheet was flexible and robust despite the absence of any traditional plasticizer in the composition. The roll was examined and it was perceived that the addition of starch to the composition served to further reduce tack. It was observed that silicate, too, could serve this role. The addition of starch and silicate was observed to be desirable to avoid tack in extreme climactic conditions.

Example L

Sheet from the Example K was cut and stacked in a plastic hockey puck style container. Bruton's snuff tobacco was sprinkled into the container. The added lose tobacco was found to make the container deliciously aromatic when opened. Additionally, the container was exposed to extreme temperature and humidity with no observed tack of the sheet pieces. This was attributed to the role of the loose tobacco in maintaining separation between the pieces.

Example M

Pieces of 350 mg piece weight were cut from Example A were folded in half to test disintegration time in the buccal cavity in four healthy volunteers. Disintegration in the buccal cavity took from sixty-five to eighty minutes.

Example N

A test was performed to determine to determine whether the pH stability of the product. The sheet of example A was dissolved—10 g of sheet in a 20 gram bottle of water. Using an Oakton pH meter, the pH was determined to be 6.8. The same material was tested in the same fashion two months later and the result was 6.71.

Example O

Six pounds of the composition below were mixed and extruded in accordance with the process of Example A. A test was performed to determine the effect on pH of compositions including sodium bicarbonate. pH was determined to be 7.34.

| Ingredient | % | Supplier |
|---|---|---|
| HPC LF | 53 | Aqualon (Hercules) |
| Propylene Glycol FCC, NF | 3 | Spectrum |
| Xylitol NF | 5.25 | Roquette |
| Bitter Masker | 2 | Ungerer |
| Sucralose | 2 | Tate & Lyle |
| Snuff | 25 | Bruton |
| Cherry | 4 | Tobacco Technology |
| Red # 40 | .75 | Colorcon |
| Sodium Bicarbonate | 1 | Armin Hammer |
| TiO2 | 2 | DNP |
| Citric Acid | 1 | |
| Glycerin | 1 | |
| Total | 100 | |

Example P

Tension/Tear Tests

Samples from Example A were clipped an upper end into a heavy duty binder clip attached to a bottom hook of a Baker 0-25 lb. spring scale and clipped at a lower end in another heavy duty binder clip. The heavy duty binder clip to which the bottom of the test sample was clipped was pulled slowly with gage set to 10 lb. until failure (tear) of the sample product. A Listerine PocketPaks® Breath Strips (Cool Mint) (just purchased) failed at 0.5 pounds, a Cough, Cold and Allergy strip produced by Monosol Rx, LLC failed at 0.25 lbs., while a tobacco/NICOTINE sheet according to the present invention failed at 7.5 lbs.

One of the main reasons these tension results are so important, is that a lack of tension strength, as shown in two of the sample comparative products, is very problematic in slitting and packaging. If the roll snaps, the manufacturing line comes to a stop. A proper product, such as that of the present invention, should have sufficient tear resistance to hold up under slitting and packaging.

Example Q

Bioavailability of Nicotine in Tobacco Buccal Sheet of the Present Invention vs. Bioavailability of Nicotine in Nulife Chewettes:

This example utilized sheets of Example A containing 75 mg of tobacco.

Nicotine absorption from smokeless tobacco is widely considered to be a critical component of tobacco satisfaction. Nicotine uptake from smokeless tobacco has been widely studied. Most public health experts believe that Swedish SNUS style smokeless tobacco provides the best nicotine absorption of the currently marketed smokeless tobacco products. "The relatively high nicotine delivery of Swedish snus is similar to a cigarette, and much higher than most existing nicotine replacement therapies including nicotine gum, lozenge, inhaler and nasal spray." (See "Is Low-nicotine Marlboro snus really snus," Jonathan Foulds and Helena Furberg, Harm Reduction Journal 2008 5:9).

Leading SNUS maker Swedish Match has incorporated a study of nicotine absorption performed by Erik Lunell and Marienne Lunell as part of its Gothiatek standard. The Lunell study is entitled, "Steady state nicotine plasma levels following use of four different types of Swedish Snus compared with a 2-mg Nicorette® chewing gum: crossover study." (Nicotine & Tobacco Research Volume 7, Number 3 (June 2005) 397-403).

Figure 7:
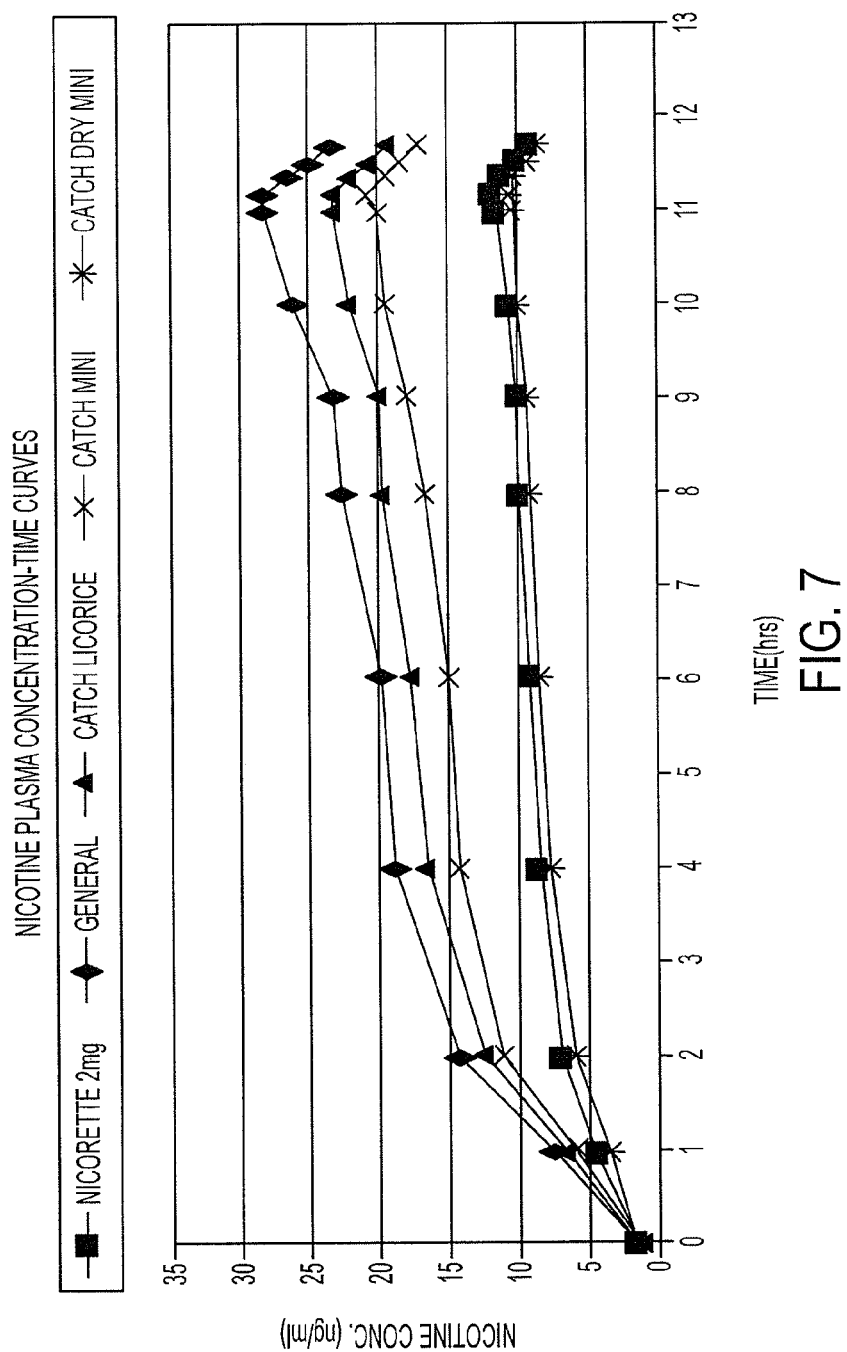
FIG. 7 is a graph showing nicotine plasma concentration vs. time curves obtained on consumption of four different snus brands and a 2 mg nicotine chewing gum according to the Gothiatek cited Lunell study.

In the Gothiatek cited Lunell study, patients take—once each hour for twelve hours—one of four different strengths of Swedish SNUS, and at a different interval, a 2 mg nicotine gum. The resulting nicotine plasma concentration curve is shown in FIG. 7.

The Lunell study demonstrates that nicotine absorption from the 2 mg gum virtually mirrors the nicotine absorption from a "Catch Dry Mini." Catch Dry Mini is SNUS pouch containing 300 mg of tobacco (See Lunell). Nicotine plasma levels were nearly doubled over the 2 mg gum by the Catch Licorice that contains 800 mg of tobacco.

To test the present invention, a single dose study (as distinguished from the Lunell study which dosed patients each hour with an additional dose) was performed on six patients to compare the nicotine absorption from a tobacco sheet containing 75 mg of tobacco with a 2 mg gum. The nicotine plasma concentration time curve is shown in FIG. 8.

More particularly, an open label, randomized, two-treatment, two-period, two-sequence, single dose, crossover comparative bioavailability study was conducted of nicotine of a tobacco product sheet of the present invention compared with that of Nulife Chewettes (containing Nicotine Polacrilex USP equivalent to Nicotine 2 mg) of Ceejay Healthcare Private Ltd., India (In technical collaboration with Positive Healthcare LLC, New York, USA) with at least seven days washout period between each administration in six healthy, adult, human male subjects under fed conditions.

Investigational Product(s):
Test: Single oral dose of tobacco buccal sheet of the present Invention (hereinafter designated "FT-TBF') 75 mg.
Reference: Single oral dose of Nulife Chewettes (containing Nicotine Polacrilex USP equivalent to Nicotine 2 mg) Manufactured by Ceejay Healthcare Private Ltd., India (In technical collaboration with Positive Healthcare LLC, New York, USA).

This study was conducted in compliance with 1CH—Guidelines for Good Clinical Practices, Indian Good Clinical Practices Guidelines (2005), ICMR—Ethical Guidelines for Biomedical Research on Human Participants (2006) and the principles enunciated in the Declaration of Helsinki (WMA General Assembly, Tokyo 2004).

The objectives of the study were (1) to investigate the comparative bioavailability of nicotine in the two products in healthy, adult, human male subjects under fed conditions, and (2) to monitor clinical status, adverse events, assess relative safety and tolerance of FT-TBF and Nulife Chewettes. Healthy, adult, male volunteers were selected from the panel of volunteers and were screened for inclusion in the study including demography, medical, personal & family history, and general examination. Furthermore, laboratory investigations such as X ray chest, ECG, hematological, biochemical, serological & urinary analysis were performed as part of screening procedures. Pre-Check in assessment was performed on the selected healthy volunteers. Alcohol breath analysis and drugs of abuse tests were conducted in all the selected subjects. All subjects were healthy as determined by medical/medication history, physical examination, laboratory investigations, ECG and X-Ray and who fulfilled the inclusion and exclusion criteria for the study.

A standard food was provided to all the subjects 2 hours before the dosing time. Subjects were prohibited from smoking/alcohol/carbonated drinks/grapefruit or grapefruit containing products/xanthine containing products throughout the duration of the study. Subjects were not allowed to eat or drink for 15 minutes before and after dosing. A single dose of 75 mg of FT-TBF or 2 mg of Nulife Chewettes was administered to the subjects at 9:30 AM on May 4, 2008 in period I and Dec. 4, 2008 in period II. The subjects who received the test product in one study period have received the reference product in the other period as per the randomization schedule. There was a washout period of seven days between the two periods. In each period, a total of 14 blood samples (1×5 ml each) were collected at 00.00 hour (pre-dose), 00.08, 00.16, 00.25, 00.50, 00.75, 01.00, 01.25, 01.50, 02.00, 03.00, 04.00, 06.00 and 08.00 hours post-dose. The total volume of blood withdrawn per subject in this study was about 166 ml. After collection, blood samples were centrifuged at 3000 rpm for 10 minutes at 4° C. to separate the plasma. All plasma samples were aliquoted into duplicates (2 sets) and stored at −20° C. The first 1 ml of the plasma samples were collected in the first aliquot and the remaining quantity of the plasma sample were collected in the second aliquot. All the subjects were monitored for any adverse event.

The analytes Nicotine, Cotinine and internal standard Metoprolol were extracted from 0.250 mL aliquot of human EDTA plasma by solid phase extraction method using Phenomenex Strata-X 33Jm, 30 mg/1 mL SPE cartridges. The samples were injected into a liquid chromatography coupled with mass spectroscopy (LC-MS/MS) using Phenomenex Luna HILIC 200A, 100×2 mm, 5J column. The mobile phase consisted of mixture of 10 mM Ammonium formate buffer (pH 3.5): Acetonitrile (10:90). Quantitation was by peak area ratio method. A weighted (1/×2) linear regression was performed to determine the concentration of analytes.

A single oral dose of tobacco buccal sheet of the present invention (FT-TBF) or Nulife chewettes was administered in each period. The treatment phases were separated by a washout period of seven days between each drug administration.

All the subjects were allocated to two treatments. Following administration of FT-TBF, all the subjects retained the sheet until it is dissolved completely. It took 19-34 minutes for the sheet to dissolve completely. Upon conclusion of the clinical phase of the study, vital signs measurements and post-study laboratory tests confirmed the absence of significant changes in the subject's state of health. Both formulations were well tolerated and there were no relevant differences in safety profiles observed between the preparations.

The sample analysis was carried out using mass spectroscopy (LC-MS/MS). Throughout the study the subjects had normal vitals and no allergic reactions were reported.

Upon analysis of data, it was observed that the Test Product (FT-TBF) shows better bioavailability profile than the Reference Product (R) Nulife Chewettes (containing Nicotine Polacrilex USP equivalent to Nicotine 2 mg) of Ceejay Healthcare Private Ltd., India. The PK parameters of Nicotine for Test and Reference for $C_{max}$, $AUC_t$ and $AUC_{inf}$ are 5.66, 19.54, 27.30 and 3.89, 15.30, 22.87, respectively. The PK parameters of Cotinine for Test and Reference for Cmax, $AUC_t$ and $AUC_{inf}$ are 19.34, 112.41, 886.01 and 15.37, 87.01, 233.17 respectively. The Vz (Volume of Distribution) of Test and Reference for Nicotine and Cotinine are 14260188.25, 488454.45 and 4319888.30, 127879.28 respectively and even the clearance (Cl) also depicts a better profile of Test and Reference for Nicotine and Cotinine such as 3378838.03, 110488.18 and 153492.40, 9106.64 respectively. In the foregoing:

$C_{max}$=Maximum measured plasma concentration over the time span specified.

$AUC_t$=the area under the plasma concentration versus time curve, from time 0 to the last measurable concentration, as calculated by the linear trapezoidal method.

$AUC_{inf}$=the area under the plasma concentration versus time curve from time 0 to infinity. AUC0-° is calculated as the sum of AUC0-t plus the ratio of the last measurable plasma concentration to the elimination rate constant.

$AUC_{Extrap}$=the extrapolated area under the plasma concentration versus time VZ Volume of distribution based on the terminal phase Cl=Total body clearance and is calculated as CL=Dose/AUC MRTlast=Mean Residence Time when the drug concentration profile is not extrapolated to infinity, but rather is based on values up to and including the last measured concentration: MRTlast=AUMClast/AUClast MRTINF=Mean Residence Time when the drug concentration profile is extrapolated to infinity AUMClast=Area under the moment curve computed to the last observation.

TBF=Tobacco Buccal Film (sheet)

CRF=Case Report Form

AE=Adverse Event

ANOVA=Analysis of Variance

The mean of the concentration of nicotine in all of the subjects' blood is plotted vs. time in FIG. 8 for the sample of the present invention (curve 40) and the reference sample (curve 41).

The 75 mg tobacco sheet of the present invention had a mean $C_{max}$ (maximum plasma concentration) of 5.66 as compared with a mean $C_{max}$ for the 2 mg gum of 3.89—exceeding the reference gum by 30%. The 75 mg tobacco sheet had a mean $AUC_{inf}$ (area under the plasma concentration versus time curve from zero to infinity) of 27.30 as compared with a mean $AUC_{inf}$ for the 2 mg gum of 22.87—exceeding the reference gum by 16%.

The implication of this study is the dramatic enhancement of the nicotine bioavailability of tobacco contained in the presently invented sheet. A 75 mg sheet delivered substantially more nicotine than a 2 mg nicotine gum, whereas the Lunell study indicates that a 300 mg SNUS pouch merely mimics a 2 mg nicotine gum for nicotine delivery.

Example R

Ten pieces of Nicorette, 1.2 gm each were soaked in water to soak off the chickle coating; after soaking off the chickle coating, each piece was now 1 gm each, thus all ten totaled 10 gm. This 10 gm was added to 30 gm of the starting composition of Example A, thoroughly mixed and heated to form a sheet between two pieces of cold foil. As a control example, 10 gm of the starting composition of Example A was made into a sheet. 500 mg pieces were then cut of both. The control example A was sucked for 5 minutes and weight was down to 155 mg. At 7 minutes, a control trace was present. Then a suck test was done on 500 mg Nicorette (25% or 125 mg. is gum base) and at 5 minutes it weighed 277 mg., at 7 minutes 261 mg., and at 10 minutes 237 mg. It was therefore concluded that the insoluble polymer used in Nicorette, polacrilex, will lengthen the dissolution time because it is not water soluble.

The test was repeated with 500 mg of the control example to obtain the following results:

| | |
|---|---|
| 2 minutes suck test: | 462 mg. |
| 4 minutes: | 301 mg. |
| 5 minutes: | 119 mg. |
| 7 minutes: | trace. |

The test was repeated with 500 mg of this Example P with insoluble polymer (poiacrilex) and (125 mg. gum base):

| | |
|---|---|
| 2 minutes: | 470 mg. |
| 4 minutes: | 370 mg. |
| 5 minutes: | 310 mg. |
| 7 minutes: | 275 mg. |
| 10 minutes: | 230 mg. |

It is concluded that the insoluble polymer will lengthen the time for dissolution. It will also convey particulate unwanted taste. (Polacrilex is a highly purified crosslinked polyacrylic copolymer supplied in Hydrogen form. This polymer has the following technical characteristics:

| | |
|---|---|
| Type of Resin: | Weak acid cation exchange resin |
| Matrix structure: | Crosslinked polyacrylic copolymer |
| Functional group: | Carboxylic |
| Physical form: | White to off-white fine free flowing powder |
| Ionic form: | Hydrogen |
| Particle size (US mesh): | +100-0% <br> +200-15% max. <br> −200-85% min. |
| Total Exchange Capacity: | 10.0 meq/dry gram (min) |
| Solubility: | Insoluble in all common solvents.) |

Example S

Five pounds of the starting composition of Example A were mixed in the same method as example A. The same process conditions were used to extrude a sheet, except the die was full opened and the take off rollers were slowed down. This had the effect of increasing the thickness of the sheet to 25 mils. It was observed that the composition could be made still thicker by an increase in the rpm of the screw from 180 rpm. One inch square pieces were cut and took approximately 45 minutes to dissolve. The roll was found to be flexible when made and after 90 days exposure to ambient conditions.

Example T

Roll stock made through the composition and process of Example A and was chipped up into small pieces using a conventional. Three pounds of the composition of Example A was then mixed, including 30% of the chipped material. This new material was then extruded in accordance with the process parameters of Example A. The extruded roll stock was excellent and not distinguishable from the roll stock made in accordance with Example A. Thus, it was observed that the process of the present invention supports re-use of waste materials.

Example U

One pound of the starting composition of Example A was mixed by the same method as Example A. The mix was pressed between two pieces of aluminum foil. The foil sandwiched material was sandwiched between a hot plate at 325 Fahrenheit and a hot iron, which was pressed down on the sandwich. The heat and pressure melted the composition into a sheet. The resulting sheet was uneven in thickness, with an average thickness of 30 mils and was flexible.

Example V

Samples of the extruded composition of Example A were sent to a validated, third party lab in order to test their nicotine concentration. The results were as follows:

| | | Matrix Code | | | |
|---|---|---|---|---|---|
| | | WT | WT | WT Sample 1D | WT |
| Tobacco Constituent | Unit | 082516 Average | 082516 Std. Dev. | 082516 L. Limit (95%) | 082516 U. Limit (95%) |
| Nicotine | (µg/g) | 3846 | 154 | 3655 | 4038 |
| Nornicotine | (µg/g) | NQ | NQ | N/A | N/A |
| Anabasine | (µg/g) | NQ | NQ | N/A | N/A |
| Myosmine | (µg/g) | BDL | BDL | N/A | N/A |
| Anatabine | (µg/g) | 58.5 | 1.6 | 56.5 | 60.6 |

A review of these results demonstrates the excellent content uniformity of the pieces, as manifested in the standard deviation of nicotine concentration.

I claim:

1. An extruded bioactive product comprising a sheet made by extruding or hot melt shaping a nonaqueous composition comprising at least one thermoplastic polymer, an ion exchange resin and a bioactive agent other than tobacco, the composition not containing polycarbophil, the sheet comprising a matrix comprising the at least one thermoplastic polymer and an ion exchange resin and bioactive agent complex distributed in the matrix, the matrix being soluble in the mucosa of a user and resulting in sustained release of the bioactive agent to the user.

2. The extruded bioactive product according to claim 1, wherein the sheet has a rectangular shape.

3. The extruded bioactive product according to claim 1, wherein the at least one polymer comprises hydroxypropyl cellulose (HPC).

4. The extruded bioactive product according to claim 1, wherein the bioactive is in the form of a nonaqueous liquid.

5. The extruded bioactive product according to claim 1, further comprising a mucosal absorbing enhancer.

6. The extruded bioactive product according to claim 5, wherein the sheet has an average dissolution time of 5 to 50 minutes and a thickness of approximately 10-50 mil, to dissolve in the oral cavity.

7. The extruded bioactive product according to claim 1, further comprising a buffering agent for controlling a pH of the composition.

8. The extruded bioactive product according to claim 7, wherein the buffering agent is present in an amount to provide the product with a pH of 2.5 to 9 when the composition is present in the user's mouth.

9. The extruded bioactive product according to claim 1, wherein the bonds between the bioactive agent and the ion exchange resin are substantially intact.

10. The extruded bioactive product according to claim 1, wherein the ratio of ion exchange to bioactive agent exceeds 3 to 1 (wt/wt).

11. The extruded bioactive product according to claim 1, wherein the bioactive product is in the form of a sheet having a thickness greater than 10 mil.

12. The extruded bioactive product according to claim 1, wherein the bioactive agent includes chitosan.

13. The extruded bioactive product according to claim 1, wherein the extruded composition includes less than 6 wt % water.

14. The extruded bioactive product according to claim 1, further comprising a flavoring.

15. The extruded bioactive product according to claim 1, further comprising a plasticizer.

16. The extruded bioactive product according to claim 1, wherein the sheet has a tensile strength of at least 4 lbs.

17. The extruded bioactive product according to claim 1, wherein the sheet has a uniformity in the range of +−10%.

18. The extruded bioactive product according to claim 1, wherein the at least one thermoplastic polymer is contained in an amount of at least 20 wt % of the whole composition.

19. The extruded bioactive product according to claim 1, wherein the at least one thermoplastic polymer comprises a water soluble polymer.

20. The extruded bioactive product according to claim 1, wherein the bioactive includes nicotine.

\* \* \* \* \*